(12) United States Patent
Schoenefeld et al.

(10) Patent No.: US 9,439,659 B2
(45) Date of Patent: Sep. 13, 2016

(54) PATIENT-SPECIFIC SACROILIAC GUIDES AND ASSOCIATED METHODS

(71) Applicant: Biomet Manufacturing, LLC, Warsaw, IN (US)

(72) Inventors: Ryan J. Schoenefeld, Fort Wayne, IN (US); Robert C. Gutierrez, Huntington Beach, CA (US); Philip A. Mellinger, Ladera Ranch, CA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/753,560

(22) Filed: Jun. 29, 2015

(65) Prior Publication Data
US 2015/0374389 A1 Dec. 31, 2015

Related U.S. Application Data

(63) Continuation of application No. 13/221,968, filed on Aug. 31, 2011, now Pat. No. 9,066,734.

(51) Int. Cl.
*A61B 17/17* (2006.01)
*A61B 17/70* (2006.01)
(Continued)

(52) U.S. Cl.
CPC ....... *A61B 17/1757* (2013.01); *A61B 17/7055* (2013.01); *A61B 2017/0042* (2013.01); *A61B 2017/568* (2013.01)

(58) Field of Classification Search
CPC .............. A61B 17/17; A61B 17/1703; A61B 17/1739; A61B 17/1742; A61B 17/1746; A61B 17/175; A61B 17/1753; A61B 17/1757; A61B 17/176; A61B 17/1764; A61B 17/1767

USPC ................ 606/86 A, 86 R–89, 96, 104, 246, 606/250–278; 623/17.11–17.16
See application file for complete search history.

(56) References Cited

U.S. PATENT DOCUMENTS

| | | |
|---|---|---|
| 1,480,285 A | 1/1924 | Moore |
| 2,181,746 A | 11/1939 | Siebrandt |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

"Amazing Precision. Beautiful Results. The next evolution of MAKOplasty.RTM. is here," brochure. (Feb. 2009) MAKO Surgical Corp. 6 pages.

(Continued)

*Primary Examiner* — Christian Sevilla
*Assistant Examiner* — Eric S Gibson
(74) *Attorney, Agent, or Firm* — Schwegman Lundberg & Woessner, P.A.

(57) ABSTRACT

A patient-specific alignment guide includes a patient-specific portion and a guiding element having a through opening. The patient-specific portion has a patient-specific surface preoperatively configured to mate as a negative of a portion of an iliac crest of a pelvis of a specific patient and mate to the iliac crest only in one position. The guiding element has a preoperatively configured orientation and location relative to the patient-specific portion for preparing a bore in the bone of the patient to direct a bone screw at the preoperatively configured orientation and location for sacroiliac fixation.

17 Claims, 11 Drawing Sheets

(51) Int. Cl.
 *A61B 17/00* (2006.01)
 *A61B 17/56* (2006.01)

(56) References Cited

U.S. PATENT DOCUMENTS

| | | | |
|---|---|---|---|
| 2,407,845 A | 9/1946 | Nemeyer | |
| 2,416,228 A | 2/1947 | Sheppard | |
| 2,618,913 A | 11/1952 | Plancon et al. | |
| 2,910,978 A | 11/1959 | Urist | |
| 3,330,611 A | 7/1967 | Heifetz | |
| 3,840,904 A | 10/1974 | Tronzo | |
| 3,975,858 A | 8/1976 | Much | |
| 4,246,895 A | 1/1981 | Rehder | |
| 4,306,866 A | 12/1981 | Weissman | |
| 4,324,006 A | 4/1982 | Charnley | |
| 4,421,112 A | 12/1983 | Mains et al. | |
| 4,436,684 A | 3/1984 | White | |
| 4,457,306 A | 7/1984 | Borzone | |
| 4,475,549 A | 10/1984 | Oh | |
| 4,506,393 A | 3/1985 | Murphy | |
| 4,524,766 A | 6/1985 | Petersen | |
| 4,528,980 A | 7/1985 | Kenna | |
| 4,565,191 A | 1/1986 | Slocum | |
| 4,619,658 A | 10/1986 | Pappas et al. | |
| 4,621,630 A | 11/1986 | Kenna | |
| 4,632,111 A | 12/1986 | Roche | |
| 4,633,862 A | 1/1987 | Petersen | |
| 4,663,720 A | 5/1987 | Duret et al. | |
| 4,689,984 A | 9/1987 | Kellner | |
| 4,695,283 A | 9/1987 | Aldinger | |
| 4,696,292 A | 9/1987 | Heiple | |
| 4,703,751 A | 11/1987 | Pohl | |
| 4,704,686 A | 11/1987 | Aldinger | |
| 4,706,660 A | 11/1987 | Petersen | |
| 4,719,907 A | 1/1988 | Banko et al. | |
| 4,721,104 A | 1/1988 | Kaufman et al. | |
| 4,722,330 A | 2/1988 | Russell et al. | |
| 4,759,350 A | 7/1988 | Dunn et al. | |
| 4,778,474 A | 10/1988 | Homsy | |
| 4,800,874 A | 1/1989 | David et al. | |
| 4,821,213 A | 4/1989 | Cline et al. | |
| 4,822,365 A | 4/1989 | Walker et al. | |
| 4,841,975 A | 6/1989 | Woolson | |
| 4,846,161 A | 7/1989 | Roger | |
| 4,871,975 A | 10/1989 | Nawata et al. | |
| 4,892,545 A | 1/1990 | Day et al. | |
| 4,893,619 A | 1/1990 | Dale et al. | |
| 4,896,663 A | 1/1990 | Vandewalls | |
| 4,907,577 A * | 3/1990 | Wu | A61B 17/1757 606/104 |
| 4,927,422 A | 5/1990 | Engelhardt | |
| 4,936,862 A | 6/1990 | Walker et al. | |
| 4,952,213 A | 8/1990 | Bowman et al. | |
| 4,959,066 A | 9/1990 | Dunn et al. | |
| 4,976,737 A | 12/1990 | Leake | |
| 4,979,949 A | 12/1990 | Matsen, III et al. | |
| 4,985,037 A | 1/1991 | Petersen | |
| 5,002,579 A | 3/1991 | Copf et al. | |
| 5,006,121 A | 4/1991 | Hafeli | |
| 5,007,936 A | 4/1991 | Woolson | |
| 5,030,219 A | 7/1991 | Matsen, III et al. | |
| 5,030,221 A | 7/1991 | Buechel et al. | |
| 5,041,117 A | 8/1991 | Engelhardt | |
| 5,053,037 A | 10/1991 | Lackey | |
| 5,053,039 A | 10/1991 | Hofmann et al. | |
| 5,056,351 A | 10/1991 | Stiver et al. | |
| 5,086,401 A | 2/1992 | Glassman et al. | |
| 5,098,383 A | 3/1992 | Hemmy et al. | |
| 5,098,436 A | 3/1992 | Ferrante et al. | |
| 5,102,412 A * | 4/1992 | Rogozinski | A61B 17/7082 606/250 |
| 5,108,425 A | 4/1992 | Hwang | |
| 5,122,144 A | 6/1992 | Bert et al. | |
| 5,123,927 A | 6/1992 | Duncan et al. | |
| 5,129,908 A | 7/1992 | Petersen | |
| 5,129,909 A | 7/1992 | Sutherland | |
| 5,133,660 A * | 7/1992 | Fenick | A61C 1/084 433/173 |
| 5,133,760 A | 7/1992 | Petersen et al. | |
| 5,140,777 A | 8/1992 | Ushiyama et al. | |
| 5,141,512 A * | 8/1992 | Farmer | A61B 17/1746 606/87 |
| 5,150,304 A | 9/1992 | Berchem et al. | |
| 5,176,684 A | 1/1993 | Ferrante et al. | |
| 5,194,066 A | 3/1993 | Van Zile | |
| 5,234,433 A | 8/1993 | Bert et al. | |
| 5,242,444 A * | 9/1993 | MacMillan | A61B 17/1757 606/60 |
| 5,246,444 A | 9/1993 | Schreiber | |
| 5,253,506 A | 10/1993 | Davis et al. | |
| 5,258,032 A | 11/1993 | Bertin | |
| 5,261,915 A | 11/1993 | Durlacher et al. | |
| 5,274,565 A | 12/1993 | Reuben | |
| 5,282,802 A | 2/1994 | Mahony, III | |
| 5,299,288 A | 3/1994 | Glassman et al. | |
| 5,300,077 A | 4/1994 | Howell | |
| 5,306,275 A * | 4/1994 | Bryan | A61B 17/1757 606/250 |
| 5,320,529 A * | 6/1994 | Pompa | A61C 1/084 433/214 |
| 5,320,625 A | 6/1994 | Bertin | |
| 5,323,697 A | 6/1994 | Schrock | |
| 5,334,203 A * | 8/1994 | Wagner | A61B 17/7052 24/396 |
| 5,334,205 A * | 8/1994 | Cain | A61B 17/1742 606/86 R |
| 5,342,366 A | 8/1994 | Whiteside et al. | |
| 5,344,423 A | 9/1994 | Dietz et al. | |
| 5,360,431 A * | 11/1994 | Puno | A61B 17/7037 606/265 |
| 5,360,446 A | 11/1994 | Kennedy | |
| 5,364,402 A | 11/1994 | Mumme et al. | |
| 5,368,858 A | 11/1994 | Hunziker | |
| 5,370,692 A | 12/1994 | Fink et al. | |
| 5,370,699 A | 12/1994 | Hood et al. | |
| 5,405,395 A | 4/1995 | Coates | |
| 5,408,409 A | 4/1995 | Glassman et al. | |
| 5,411,521 A | 5/1995 | Putnam et al. | |
| 5,415,662 A | 5/1995 | Ferrante et al. | |
| 5,417,694 A | 5/1995 | Marik et al. | |
| D359,557 S * | 6/1995 | Hayes | D24/140 |
| 5,438,263 A | 8/1995 | Dworkin et al. | |
| 5,440,496 A | 8/1995 | Andersson et al. | |
| 5,448,489 A | 9/1995 | Reuben | |
| 5,449,360 A | 9/1995 | Schreiber | |
| 5,452,407 A | 9/1995 | Crook | |
| 5,454,816 A | 10/1995 | Ashby | |
| 5,462,550 A | 10/1995 | Dietz et al. | |
| 5,472,415 A | 12/1995 | King et al. | |
| 5,474,559 A * | 12/1995 | Bertin | A61B 17/154 606/86 R |
| 5,490,854 A | 2/1996 | Fisher et al. | |
| 5,496,324 A | 3/1996 | Barnes | |
| 5,507,833 A | 4/1996 | Bohn | |
| 5,514,519 A | 5/1996 | Neckers | |
| 5,520,695 A | 5/1996 | Luckman | |
| 5,527,317 A | 6/1996 | Ashby et al. | |
| 5,539,649 A | 7/1996 | Walsh et al. | |
| 5,540,695 A | 7/1996 | Levy | |
| 5,545,222 A | 8/1996 | Bonutti | |
| 5,549,688 A | 8/1996 | Ries et al. | |
| 5,554,190 A | 9/1996 | Draenert | |
| 5,560,096 A | 10/1996 | Stephens | |
| 5,571,110 A | 11/1996 | Matsen, III et al. | |
| 5,578,037 A | 11/1996 | Sanders et al. | |
| 5,593,411 A | 1/1997 | Stalcup et al. | |
| 5,595,703 A | 1/1997 | Swaelens et al. | |
| 5,601,565 A | 2/1997 | Huebner | |
| 5,607,431 A | 3/1997 | Dudasik et al. | |
| 5,611,802 A | 3/1997 | Samuelson et al. | |
| 5,613,969 A | 3/1997 | Jenkins, Jr. | |
| 5,620,448 A | 4/1997 | Puddu | |
| 5,634,927 A | 6/1997 | Houston et al. | |
| 5,641,323 A | 6/1997 | Caldarise | |

(56) References Cited

U.S. PATENT DOCUMENTS

| | | |
|---|---|---|
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliott et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,766,251 A | 6/1998 | Koshino et al. |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A * | 11/1999 | Masini ............... A61B 17/1746 606/91 |
| 5,980,526 A | 11/1999 | Johnson et al. |
| 6,008,433 A | 12/1999 | Stone |
| 6,019,767 A | 2/2000 | Howell |
| 6,033,415 A | 3/2000 | Mittelstadt et al. |
| 6,042,612 A | 3/2000 | Voydeville |
| 6,056,754 A | 5/2000 | Haines et al. |
| 6,059,789 A | 5/2000 | Dinger et al. |
| 6,059,833 A | 5/2000 | Doets |
| 6,066,142 A * | 5/2000 | Serbousek ......... A61B 17/1728 606/70 |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,165,223 A | 12/2000 | Metzger et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,888 B1 | 10/2001 | Mellinger et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 * | 12/2001 | Franklin ............... A61B 19/201 600/429 |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,413,279 B1 | 7/2002 | Metzger et al. |
| 6,424,332 B1 | 7/2002 | Powell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,524,312 B2 * | 2/2003 | Landry ............... A61B 17/1757 606/279 |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,589,283 B1 | 7/2003 | Metzger et al. |
| 6,591,581 B2 | 7/2003 | Schmieding |
| 6,605,293 B1 | 8/2003 | Giordano et al. |
| 6,610,067 B2 | 8/2003 | Tallarida et al. |
| 6,616,668 B2 | 9/2003 | Altarac et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |

(56) References Cited

U.S. PATENT DOCUMENTS

| | | |
|---|---|---|
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,949,123 B2 * | 9/2005 | Reiley ............... A61B 17/1671 606/248 |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S * | 12/2006 | Buttler ......................... D24/133 |
| 7,166,111 B2 * | 1/2007 | Kolb ................ A61B 17/1728 606/96 |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,232,441 B2 * | 6/2007 | Altarac ............. A61B 17/7055 606/250 |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,291,177 B2 | 11/2007 | Gibbs |
| 7,294,129 B2 * | 11/2007 | Hawkins ............ A61B 17/7037 606/86 A |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,338,527 B2 * | 3/2008 | Blatt ................ A61B 17/1757 606/247 |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma de La Barrera |
| 7,396,360 B2 * | 7/2008 | Lieberman ......... A61B 17/1757 606/104 |
| 7,427,200 B2 | 9/2008 | Noble et al. |
| 7,427,272 B2 | 9/2008 | Richard et al. |
| 7,465,320 B1 | 12/2008 | Kito et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'Neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,588,578 B2 * | 9/2009 | Triplett ............. A61B 17/1757 33/512 |
| 7,591,821 B2 | 9/2009 | Kelman |
| 7,601,155 B2 | 10/2009 | Petersen |
| 7,603,192 B2 | 10/2009 | Martin et al. |
| 7,604,638 B2 * | 10/2009 | Jacene ................ A61B 17/808 606/71 |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,674,100 B2 | 3/2010 | Hayes-Pankhurst et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,699,876 B2 | 4/2010 | Barry et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,040 B2 | 11/2010 | Ward et al. |
| 7,837,690 B2 | 11/2010 | Metzger |
| 7,846,382 B2 | 12/2010 | Strand et al. |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Rossner et al. |
| 8,043,290 B2 * | 10/2011 | Harrison ............. A61B 17/66 606/60 |
| 8,062,301 B2 | 11/2011 | Ammann et al. |

(56) References Cited

U.S. PATENT DOCUMENTS

| | | |
|---|---|---|
| 8,066,708 B2 | 11/2011 | Lang et al. |
| 8,070,752 B2 * | 12/2011 | Metzger ............... A61B 17/154 606/86 R |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,177,785 B2 * | 5/2012 | Vaidya .................. A61B 17/68 606/60 |
| 8,182,489 B2 | 5/2012 | Horacek |
| 8,187,302 B2 * | 5/2012 | Henderson, Sr. .. A61B 17/7055 606/246 |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,428 B2 * | 7/2012 | Trieu .................. A61B 17/7055 606/104 |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'Neill et al. |
| 8,268,100 B2 | 9/2012 | O'Neill et al. |
| D669,176 S | 10/2012 | Frey |
| 8,282,642 B2 * | 10/2012 | McClintock ....... A61B 17/1757 606/86 B |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| 8,313,491 B2 | 11/2012 | Green, II et al. |
| D672,038 S * | 12/2012 | Frey .............................. D24/140 |
| 8,333,772 B2 | 12/2012 | Fox et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,635 B2 * | 3/2013 | Vaidya ............... A61B 17/68 606/286 |
| 8,398,646 B2 | 3/2013 | Metzger et al. |
| 8,403,934 B2 * | 3/2013 | Angibaud ........... A61B 17/155 606/87 |
| 8,407,067 B2 | 3/2013 | Uthgenannt et al. |
| 8,414,594 B2 * | 4/2013 | Berger ............... A61B 17/1728 606/104 |
| 8,419,741 B2 | 4/2013 | Carignan et al. |
| 8,425,522 B2 | 4/2013 | Bonutti |
| 8,430,882 B2 * | 4/2013 | Lowry ............... A61B 17/1671 606/86 R |
| 8,430,931 B2 | 4/2013 | Acker et al. |
| 8,439,675 B2 * | 5/2013 | De Moyer ......... A61C 13/0003 433/72 |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite et al. |
| 8,979,936 B2 | 3/2015 | White et al. |
| 9,005,297 B2 | 4/2015 | Katrana et al. |
| 9,066,734 B2 | 6/2015 | Schoenefeld et al. |
| 9,295,497 B2 | 3/2016 | Schoenefeld et al. |
| 2001/0005797 A1 | 6/2001 | Barlow et al. |
| 2001/0011190 A1 | 8/2001 | Park |
| 2001/0021876 A1 | 9/2001 | Terrill-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 * | 5/2004 | Aubin ................ A61B 17/1757 606/86 A |
| 2004/0098133 A1 | 5/2004 | Carignan et al. |

(56) References Cited

U.S. PATENT DOCUMENTS

| | | |
|---|---|---|
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1* | 8/2004 | Sanford ............... A61B 17/155 606/88 |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0215190 A1* | 10/2004 | Nguyen ............. A61B 17/1671 606/86 A |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1* | 12/2004 | Lionberger ......... A61B 17/155 606/88 |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0021148 A1* | 1/2005 | Gibbs ................. A61F 2/30724 623/22.12 |
| 2005/0027303 A1* | 2/2005 | Lionberger ........... A61B 19/20 606/102 |
| 2005/0027361 A1* | 2/2005 | Reiley ............. A61B 17/1671 623/17.11 |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1* | 6/2005 | Carignan ............ A61F 2/30942 606/96 |
| 2005/0131662 A1 | 6/2005 | Ascenzi et al. |
| 2005/0137708 A1 | 6/2005 | Clark |
| 2005/0143818 A1* | 6/2005 | Yuan ................. A61B 17/1757 623/17.11 |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203522 A1* | 9/2005 | Vaughan ........... A61B 17/1757 606/246 |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267481 A1* | 12/2005 | Carl .................... A61B 17/1642 606/79 |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1* | 5/2006 | Swaelens ............... A61C 1/084 433/76 |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1* | 6/2006 | Bennett ............. A61B 17/1764 606/87 |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161154 A1* | 7/2006 | McAfee ................. A61F 2/44 623/17.11 |
| 2006/0161165 A1 | 7/2006 | Swanson |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0229618 A1* | 10/2006 | Dube ................. A61B 17/1728 606/86 B |
| 2006/0235391 A1* | 10/2006 | Sutterlin, III ...... A61B 17/7064 606/86 A |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |

(56) References Cited

U.S. PATENT DOCUMENTS

| | | |
|---|---|---|
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0106305 A1* | 5/2007 | Kao ............ A61B 19/201 606/130 |
| 2007/0106383 A1* | 5/2007 | Abdou ............ A61B 17/70 623/17.11 |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0123872 A1* | 5/2007 | Brockmeyer ...... A61B 17/7055 606/250 |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162021 A1* | 7/2007 | Dinh ............ A61B 17/7059 606/86 A |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0225713 A1* | 9/2007 | Altarac ............ A61B 17/7052 606/64 |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1* | 12/2007 | Metzger ............ A61B 17/154 606/87 |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1* | 3/2008 | Wasielewski ............ A61B 5/03 623/18.11 |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1* | 5/2008 | Schoenefeld ...... A61B 17/1721 606/96 |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0154306 A1* | 6/2008 | Heinz ............ A61B 17/7055 606/256 |
| 2008/0161815 A1* | 7/2008 | Schoenefeld ........ A61B 17/154 606/87 |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287953 A1* | 11/2008 | Sers ............ A61C 1/084 606/87 |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1* | 1/2009 | Metzger ............ A61B 17/1764 606/88 |
| 2009/0024169 A1* | 1/2009 | Triplett ............ A61B 17/1757 606/248 |
| 2009/0043556 A1 | 2/2009 | Axelson et al. |
| 2009/0048618 A1 | 2/2009 | Harrison et al. |
| 2009/0066936 A1 | 3/2009 | Huang et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1* | 3/2009 | Lowry ............ A61B 17/1671 606/280 |
| 2009/0082770 A1 | 3/2009 | Worner et al. |
| 2009/0082774 A1 | 3/2009 | Oti et al. |
| 2009/0087276 A1 | 4/2009 | Rose |

(56) References Cited

U.S. PATENT DOCUMENTS

| | | |
|---|---|---|
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1* | 4/2009 | Aram ............... A61B 17/155 606/87 |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118764 A1* | 5/2009 | Vaughan ............ A61B 17/1757 606/246 |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0143716 A1* | 6/2009 | Lowry ............... A61B 17/8827 604/22 |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187191 A1* | 7/2009 | Carl ................. A61B 17/1642 606/80 |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259261 A1* | 10/2009 | Reiley ............... A61B 17/8897 606/329 |
| 2009/0259312 A1 | 10/2009 | Shterling et al. |
| 2009/0270868 A1 | 10/2009 | Park et al. |
| 2009/0270917 A1* | 10/2009 | Boehm ............... A61B 17/7023 606/246 |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1* | 4/2010 | Keefer ............... A61B 17/1746 606/91 |
| 2010/0082067 A1 | 4/2010 | Kondrashov |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0139377 A1 | 6/2010 | Huang et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0160925 A1* | 6/2010 | Heilala ............... A61B 17/17 606/96 |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1* | 7/2010 | White ............... A61B 17/155 606/88 |
| 2010/0198067 A1 | 8/2010 | Mahfouz et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0222783 A1* | 9/2010 | May .................. A61B 17/155 606/89 |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1* | 10/2010 | Capsal ............... A61C 1/08 606/96 |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1* | 11/2010 | Snider ............... A61B 17/175 606/89 |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1* | 1/2011 | Marino ............... A61B 17/1757 606/87 |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046631 A1* | 2/2011 | Suter ............... A61C 1/084 606/96 |
| 2011/0046735 A1 | 2/2011 | Metzger et al. |

(56) References Cited

U.S. PATENT DOCUMENTS

| | | | |
|---|---|---|---|
| 2011/0054478 A1 | 3/2011 | Vanasse et al. | |
| 2011/0066193 A1 | 3/2011 | Lang et al. | |
| 2011/0066245 A1 | 3/2011 | Lang et al. | |
| 2011/0071528 A1 | 3/2011 | Carson | |
| 2011/0071529 A1 | 3/2011 | Carson | |
| 2011/0071530 A1 | 3/2011 | Carson | |
| 2011/0071532 A1 | 3/2011 | Carson | |
| 2011/0071533 A1* | 3/2011 | Metzger | A61B 17/157 606/88 |
| 2011/0071581 A1 | 3/2011 | Lang et al. | |
| 2011/0071802 A1 | 3/2011 | Bojarski et al. | |
| 2011/0087332 A1 | 4/2011 | Bojarski et al. | |
| 2011/0092804 A1 | 4/2011 | Schoenefeld et al. | |
| 2011/0093086 A1 | 4/2011 | Witt et al. | |
| 2011/0106093 A1 | 5/2011 | Romano et al. | |
| 2011/0106254 A1 | 5/2011 | Abel et al. | |
| 2011/0125264 A1 | 5/2011 | Bagga et al. | |
| 2011/0125284 A1 | 5/2011 | Gabbrielli et al. | |
| 2011/0130795 A1 | 6/2011 | Ball | |
| 2011/0151027 A1 | 6/2011 | Clineff et al. | |
| 2011/0151259 A1 | 6/2011 | Jarman-Smith et al. | |
| 2011/0153025 A1 | 6/2011 | McMinn | |
| 2011/0160736 A1 | 6/2011 | Meridew et al. | |
| 2011/0160867 A1 | 6/2011 | Meridew et al. | |
| 2011/0166578 A1* | 7/2011 | Stone | A61B 17/151 606/88 |
| 2011/0172672 A1* | 7/2011 | Dubeau | A61B 17/151 606/87 |
| 2011/0177590 A1 | 7/2011 | Clyne et al. | |
| 2011/0184419 A1 | 7/2011 | Meridew et al. | |
| 2011/0184526 A1 | 7/2011 | White et al. | |
| 2011/0190899 A1 | 8/2011 | Pierce et al. | |
| 2011/0190901 A1 | 8/2011 | Weissberg et al. | |
| 2011/0213376 A1 | 9/2011 | Maxson et al. | |
| 2011/0214279 A1 | 9/2011 | Park et al. | |
| 2011/0218545 A1* | 9/2011 | Catanzarite | A61B 17/155 606/96 |
| 2011/0224674 A1 | 9/2011 | White et al. | |
| 2011/0238071 A1* | 9/2011 | Fernandez-Scoma | A61C 1/084 606/80 |
| 2011/0238181 A1* | 9/2011 | Trieu | A61B 17/1735 623/17.11 |
| 2011/0245835 A1 | 10/2011 | Dodds et al. | |
| 2011/0251617 A1 | 10/2011 | Ammann et al. | |
| 2011/0257657 A1 | 10/2011 | Turner et al. | |
| 2011/0264229 A1* | 10/2011 | Donner | A61F 2/30988 623/18.11 |
| 2011/0269100 A1* | 11/2011 | Furrer | A61B 17/151 433/72 |
| 2011/0270315 A1* | 11/2011 | Vaughan | A61B 17/1757 606/264 |
| 2011/0275032 A1 | 11/2011 | Tardieu et al. | |
| 2011/0276145 A1 | 11/2011 | Carignan et al. | |
| 2011/0282473 A1 | 11/2011 | Pavlovskaia et al. | |
| 2011/0295887 A1 | 12/2011 | Palmese et al. | |
| 2011/0313424 A1 | 12/2011 | Bono et al. | |
| 2011/0319745 A1* | 12/2011 | Frey | A61B 17/15 600/407 |
| 2012/0010619 A1 | 1/2012 | Barsoum | |
| 2012/0010710 A1 | 1/2012 | Frigg | |
| 2012/0010711 A1 | 1/2012 | Antonyshyn et al. | |
| 2012/0029345 A1 | 2/2012 | Mahfouz et al. | |
| 2012/0029520 A1 | 2/2012 | Lang et al. | |
| 2012/0041445 A1* | 2/2012 | Roose | A61B 17/1746 606/96 |
| 2012/0041446 A1 | 2/2012 | Wong et al. | |
| 2012/0041564 A1 | 2/2012 | Landon | |
| 2012/0065640 A1 | 3/2012 | Metzger et al. | |
| 2012/0078254 A1 | 3/2012 | Ashby et al. | |
| 2012/0078258 A1 | 3/2012 | Lo et al. | |
| 2012/0078259 A1 | 3/2012 | Meridew | |
| 2012/0089192 A1* | 4/2012 | Biedermann | A61B 17/1728 606/280 |
| 2012/0089595 A1 | 4/2012 | Jaecksch | |
| 2012/0101586 A1 | 4/2012 | Carson | |
| 2012/0109137 A1 | 5/2012 | Iannotti et al. | |
| 2012/0109138 A1 | 5/2012 | Meridew et al. | |
| 2012/0109226 A1 | 5/2012 | Iannotti et al. | |
| 2012/0116203 A1 | 5/2012 | Vancraen et al. | |
| 2012/0123422 A1* | 5/2012 | Agnihotri | A61B 17/155 606/89 |
| 2012/0130382 A1 | 5/2012 | Iannotti et al. | |
| 2012/0136365 A1 | 5/2012 | Iannotti et al. | |
| 2012/0141034 A1 | 6/2012 | Iannotti et al. | |
| 2012/0143197 A1 | 6/2012 | Lang et al. | |
| 2012/0143198 A1* | 6/2012 | Boyer | A61B 17/151 606/87 |
| 2012/0143267 A1 | 6/2012 | Iannotti et al. | |
| 2012/0150242 A1* | 6/2012 | Mannion | A61B 17/1757 606/86 A |
| 2012/0158002 A1 | 6/2012 | Carignan et al. | |
| 2012/0165954 A1 | 6/2012 | Nimal | |
| 2012/0192401 A1 | 8/2012 | Pavlovskaia et al. | |
| 2012/0196314 A1 | 8/2012 | Nawaz et al. | |
| 2012/0203236 A1* | 8/2012 | Mamourian | A61B 17/3403 606/96 |
| 2012/0209276 A1 | 8/2012 | Schuster | |
| 2012/0215225 A1 | 8/2012 | Philippon et al. | |
| 2012/0215310 A1 | 8/2012 | Sharp et al. | |
| 2012/0221017 A1 | 8/2012 | Bonutti | |
| 2012/0226283 A1* | 9/2012 | Meridew | A61B 17/1659 606/81 |
| 2012/0232596 A1 | 9/2012 | Ribeiro | |
| 2012/0245587 A1* | 9/2012 | Fang | A61B 17/1671 606/80 |
| 2012/0259335 A1* | 10/2012 | Scifert | A61B 17/155 606/80 |
| 2012/0265208 A1 | 10/2012 | Smith | |
| 2012/0271131 A1 | 10/2012 | Kling et al. | |
| 2012/0271314 A1 | 10/2012 | Stemniski et al. | |
| 2012/0271366 A1 | 10/2012 | Katrana et al. | |
| 2012/0276509 A1 | 11/2012 | Iannotti et al. | |
| 2012/0277751 A1* | 11/2012 | Catanzarite | A61B 17/155 606/88 |
| 2012/0289965 A1* | 11/2012 | Gelaude | A61B 17/15 606/87 |
| 2012/0296339 A1 | 11/2012 | Iannotti et al. | |
| 2012/0296428 A1* | 11/2012 | Donner | A61F 2/30988 623/17.11 |
| 2012/0303004 A1 | 11/2012 | Uthgenannt et al. | |
| 2012/0303033 A1 | 11/2012 | Weiner et al. | |
| 2012/0310364 A1 | 12/2012 | Li et al. | |
| 2012/0310399 A1 | 12/2012 | Metzger | |
| 2012/0316564 A1 | 12/2012 | Serbousek et al. | |
| 2012/0323246 A1 | 12/2012 | Catanzarite et al. | |
| 2012/0323282 A1 | 12/2012 | Brianza et al. | |
| 2012/0323323 A1 | 12/2012 | Vargas et al. | |
| 2013/0001121 A1 | 1/2013 | Metzger | |
| 2013/0006250 A1 | 1/2013 | Metzger et al. | |
| 2013/0018483 A1 | 1/2013 | Li et al. | |
| 2013/0035766 A1 | 2/2013 | Meridew | |
| 2013/0046310 A1 | 2/2013 | Ranawat et al. | |
| 2013/0053854 A1* | 2/2013 | Schoenefeld | A61B 17/1757 606/87 |
| 2013/0056912 A1 | 3/2013 | O'Neill et al. | |
| 2013/0060253 A1 | 3/2013 | Couture et al. | |
| 2013/0072940 A1 | 3/2013 | Dawood et al. | |
| 2013/0085500 A1 | 4/2013 | Meridew et al. | |
| 2013/0085590 A1 | 4/2013 | Bryan et al. | |
| 2013/0119579 A1 | 5/2013 | Iannotti et al. | |
| 2013/0123850 A1* | 5/2013 | Schoenefeld | A61B 17/7055 606/248 |
| 2013/0131681 A1 | 5/2013 | Katrana et al. | |
| 2013/0144392 A1 | 6/2013 | Hughes | |
| 2013/0197528 A1* | 8/2013 | Zakaria | A61B 17/155 606/88 |
| 2013/0197529 A1 | 8/2013 | Metzger et al. | |
| 2013/0197687 A1 | 8/2013 | Pavlovskaia et al. | |
| 2013/0218163 A1* | 8/2013 | Frey | A61B 5/0488 606/87 |
| 2013/0245631 A1 | 9/2013 | Bettenga | |
| 2013/0245801 A1 | 9/2013 | Schroeder | |
| 2013/0261503 A1 | 10/2013 | Sherman et al. | |
| 2013/0264749 A1 | 10/2013 | Jones et al. | |

(56) References Cited

U.S. PATENT DOCUMENTS

| | | |
|---|---|---|
| 2013/0268085 A1 | 10/2013 | Dong et al. |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, III et al. |
| 2014/0081275 A1 | 3/2014 | Metzger et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1 | 5/2014 | Maxson et al. |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 3447365 A1 | 7/1986 |
| DE | 04219939 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| GB | 2509271 A | 6/2014 |
| JP | 59157715 A | 9/1984 |
| JP | 60231208 A | 11/1985 |
| JP | 6-233790 A | 8/1994 |
| JP | 2000245758 A | 9/2000 |
| JP | 2005-218861 A | 8/2005 |
| JP | 2009514612 A | 4/2009 |
| JP | 2011505080 A | 2/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 | 5/2005 |
| TW | 201114409 A | 5/2011 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0226145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A1 | 8/2005 |
| WO | WO-2006058057 A2 | 6/2006 |
| WO | WO-2006060795 A1 | 6/2006 |
| WO | WO-2006092600 A2 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |

(56) References Cited

FOREIGN PATENT DOCUMENTS

| | | |
|---|---|---|
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013033205 A1 | 3/2013 |
| WO | WO-2013170872 A1 | 11/2013 |
| WO | WO-2014019712 A1 | 2/2014 |
| WO | WO-2014070889 A1 | 5/2014 |
| WO | WO-2015084831 A1 | 6/2015 |

OTHER PUBLICATIONS

"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (Oct. 31, 1999) 16 sheets.
"Ascent Total Knee System," brochure. Biomet, Inc. (1999) 16 sheets.
"Comprehensive.RTM. Reverse Shoulder System Surgical Technique," Biomet Orthopedics brochure (2009-2012), 48 pages.
"Comprehensive.RTM. Reverse Shoulder System Technical Design Features," Biomet Orthopedics brochure (2009), 3 pages.
"Comprehensive.RTM. Reverse Shoulder System," Biomet Orthopedics brochure (2009), 8 pages.
"Comprehensive.RTM. Shoulder System Surgical Technique," Biomet Orthopedics brochure (2007), pp. 1-53.
"Comprehensive.RTM. Total Shoulder System," Biomet Orthopedics brochure (2011), 4 pages.
"Comprehensive® Reverse Shoulder System Surgical Technique," Biomet Orthopedics brochure (2009-2012), 48 pages.
"Comprehensive® Reverse Shoulder System Technical Design Features," Biomet Orthopedics brochure (2009), 3 pages.
"Comprehensive® Reverse Shoulder System," Biomet Orthopedics brochure (2009), 8 pages.
"Comprehensive® Shoulder System Surgical Technique," Biomet Orthopedics brochure (2007), pp. 1-53.
"Comprehensive® Total Shoulder System," Biomet Orthopedics brochure (2011), 4 pages.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma.RTM. Knee System Utilizing Specialist.RTM. 2 Instrumentation," brochure. (2008) DePuy Orthopaedics, Inc. pp. 1-23.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery.RTM. Elbow System Surgical Technique," brochure. Biomet Orthopedics, Inc. (2008) pp. 1-25.
"Discovery.RTM. Elbow System," brochure. Biomet Orthopedics, Inc. (2007) 3 sheets.
"Discovery® Elbow System Surgical Technique," brochure. Biomet Orthopedics, Inc. (Dec. 31, 2008) pp. 1-25.
"Discovery® Elbow System," brochure. Biomet Orthopedics, Inc. (Nov. 30, 2007) 3 sheets.
"Hipsextant Instructions of Use." (2011) Surgical Planning Associates, Inc. 19 pages.
"Is Subchondroplasty.RTM. Right for Me?" Retrieved from <http://www.subchondroplasty.com/aboutsub.--subchondroplasty/is.sub.---subchondroplasty.sub.--right.sub.--for.sub.--> . . . Jul. 1, 2013. 1 sheet.
"Is Subchondroplasty® Right for Me?" Retrieved from <http://www.subchondroplasty.com/about_subchondroplasty/is_subchondroplasty_right_for > . . . Jul. 1, 2013. 1 sheet.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS.TM. Orthopaedic Salvage System, Femoral/Tibial Augmentation," brochure. Biomet Orthopedics, Inc., (2003) pp. 1-8 (12 sheets).
"OSS™ Orthopaedic Salvage System, Femoral/Tibial Augmentation," brochure. Biomet Orthopedics, Inc., (Mar. 31, 2004) pp. 1-8 (12 sheets).
"Patient Matched PMI Implants, C.A.M.R.A. 3-D Imaging," brochure, Biomet, Inc. (Jan. 31, 1991) 6 pages.
"Patient Matched PMI Implants, C.A.M.R.A. 3-D Imaging," brochure, Biomet, Inc. (1990) 6 pages.
"Regenerex.RTM. Tibial Cone Augment, Surgical Technique Addendum to the Vanguard.RTM. SSK Revision System," brochure. Biomet.RTM. Orthopedics. (2009) pp. 1-8 (12 sheets).
"Regenerex® Tibial Cone Augment, Surgical Technique Addendum to the Vanguard® SSK Revision System," brochure. Biomet® Orthopedics. (Mar. 31, 2010) pp. 1-8 (12 sheets).
"Signature.TM. Personalized Patient Care, Surgical Technique Addendum to the Vanguard Knee System" brochure. Biomet.RTM. Orthopedics, Inc. (2009) pp. 1-8.
"Signature™ Personalized Patient Care, Surgical Technique Addendum to the Vanguard Knee System" brochure. Biomet® Orthopedics, Inc. (May 15, 2009) pp. 1-8.
"Subchondroplasty," Retrieved from <http://www.subchondroplasty.com/>. Jul. 1, 2013. 1 sheet.
"TruMatch.TM. Personalized knee replacement solutions," tri-fold brochure. (2009) SIGMA.RTM. DePuy Orthopaedics, Inc. 2 pages.
"TruMatch™ Personalized knee replacement solutions," tri-fold brochure. (2009) SIGMA® DePuy Orthopaedics, Inc. 2 pages.

(56) References Cited

OTHER PUBLICATIONS

"Vanguard.RTM. PFR Partial Knee Patellofemoral Replacement System," Surgical Technique brochure. Biomet Orthopaedics, (2010) pp. 1-25.
"Vanguard® PFR Partial Knee Patellofemoral Replacement System," Surgical Technique brochure. Biomet Orthopaedics, (Aug. 31, 2010) pp. 1-25.
"Zimmer.RTM. UniSpacer.RTM. Knee System," brochure. (2005) Zimmer, Inc. 4 sheets.
"Zimmer® UniSpacer® Knee System," brochure. (2005) Zimmer, Inc. 4 sheets.
Biomet "Oxford.RTM. Partial Knee" brochure, 8 pages (Feb. 2011).
Biomet "Oxford® Partial Knee" brochure, 8 pages (Feb. 2011).
Biomet "The Oxford.RTM. Partial Knee Surgical Technique," brochure, pp. 1-38, (Feb. 2010).
Biomet "The Oxford® Partial Knee Surgical Technique," brochure, pp. 1-38, (Feb. 2010).
Biomet, "Oxford.RTM. Partial Knee Microplasty.RTM. Instrumentation Surgical Technique", brochure, pp. 1-54 (May 2011).
Biomet, "Oxford® Partial Knee Microplasty® Instrumentation Surgical Technique", brochure, pp. 1-54 (May 2011).
Birnbaum, Klaus, M.D., "Computer-Assisted Orthopedic Surgery With Individual Templates and Comparison to Conventional Method," Spine vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Deakon, Timothy, MD, Posterior Cruciate Ligament Reconstruction Technique Using the Modular ACL/PCL Guide Rationale and Surgical Technique, Arthrotek.RTM., a Biomet Company. (2003). (6 pages).
Deakon, Timothy, MD, Posterior Cruciate Ligament Reconstruction Technique Using the Modular ACL/PCL Guide Rationale and Surgical Technique, Arthrotek®, a Biomet Company. (2003). (6 pages).
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
European Communication Pursuant to Article 94(3) EPC mailed Jan. 22, 2015 for PCT/US2007/013223 filed Jun. 5, 2007, which claims benefit of U.S. Appl. No. 60/812,694, filed Jun. 9, 2006 and U.S. Appl. No. 11/756,057, filed May 31, 2007.
European Communication Pursuant to Article 94(3) EPC mailed Feb. 4, 2015 for PCT/US2010/024584 filed Feb. 18, 2010, which claims benefit of U.S. Appl. No. 12/389,901, filed Feb. 20, 2009.
European Communication Pursuant to Article 94(3) EPC mailed Feb. 10, 2015 for PCT/US2009/039507 filed Apr. 3, 2009, which claims benefit of U.S. Appl. No. 12/103,824, filed Apr. 16, 2008.
European Communication Pursuant to Article 94(3) EPC mailed Nov. 24, 2014 for PCT/US2012/038351 which claims benefit of U.S. Appl. No. 13/111,007, filed May 19, 2011.
Farr, J., Cole, B., Kercher, J., Batty, L. and Bajaj, S., Anteromedial Tibial Tubercle Osteotomy (Fulkerson Osteotomy). Re-print from V. Sanchis-Alfonso (ed), Anterior Knee Pain and patellar Instability, DOI: 10.1007/978-0-85729-507-1_40, © Springer-Verlag London Limited 2011.(9 pages).
Farr, J., Cole, B., Kercher, J., Batty, L. and Bajaj, S., Anteromedial Tibial Tubercle Osteotomy (Fulkerson Osteotomy). Re-print from V. Sanchis-Alfonso (ed), Anterior Knee Pain and patellar Instability, DOI:10.1007/978-0-85729-507-1.sub.--40,.COPYRGT. Springer-Verlag London Limited 2011.(9 pages).

Farr, J., Fulkerson, J. Surgical Technique for Anteromedialization of the Tibial Tubercle with the Tracker.TM. AMZ Guide System. Sports Medicine and Arthroscopy Review, vol. 2, No. 3, 1994. (12 pages).
Farr, J., Fulkerson, J. Surgical Technique for Anteromedialization of the Tibial Tubercle with the Tracker™ AMZ Guide System. Sports Medicine and Arthroscopy Review, vol. 2, No. 3, 1994. (12 pages).
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Friedman, R.J. et al., "The Use of Computerized Tomography in the Measurement of Glenoid Version", Journal of Bone & Joint Surgery Am. (JBJS) 1992;74:1032-1037 (Aug. 1992).
Great Britain Search Report mailed Dec. 21, 2011 for GB1116054. 6, claiming benefit of U.S. Appl. No. 12/888,005, filed Sep. 22, 2010.
Haaker, R.G., et al., "Minimal-invasive navigiert implantierte unikondylare Knieendoprothese," Orthopade 2006 35:1073-1079 (2006) Spinger Medizin Verlag.
Haaker, R.G., et al., "Minimal-invasive navigiert implantierte unikondyläre Knieendoprothese," Orthopäde 2006 35:1073-1079 (Sep. 13, 2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics.RTM. vol. 18, No. 2, (2003) pp. 221-229.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report and Written Opinion mailed Jan. 5, 2012 for PCT/US2010/038845 claiming benefit of U.S. Appl. No. 12/486,992, filed Jun. 18, 2009.
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Apr. 24, 2014 for PCT/US2012/059189 claiming benefit of U.S. Appl. No. 13/597,478, filed Aug, 29, 2012.
International Preliminary Report on Patentability and Written Opinion mailed Apr. 24, 2014 for PCT/US2012/059189 claiming benefit of U.S. Appl. No. 13/597,478, filed Aug. 29, 2012.
International Preliminary Report on Patentability and Written Opinion mailed Dec. 22, 2011 for PCT/US2010/038177 claiming benefit of U.S. Appl. No. 12/483,807, filed Jun. 12, 2009.
International Preliminary Report on Patentability and Written Opinion mailed Jan. 3, 2014 for PCT/US2012/042081 claiming benefit of U.S. Appl. No. 13/493,509, filed Jun. 11, 2012.
International Preliminary Report on Patentability and Written Opinion mailed Mar. 13, 2014 for PCT/US2012/052853 claiming benefit of U.S. Appl. No. 13/221,968, filed Aug. 31, 2011.
International Preliminary Report on Patentability and Written Opinion mailed May 8, 2014 for PCT/US2012/060842 claiming benefit of U.S. Appl. No. 13/653,868, filed Oct. 17, 2012.
International Preliminary Report on Patentability and Written Opinion mailed May 8, 2014 for PCT/US2012/060848 claiming benefit of U.S. Appl. No. 13/653,878, filed Oct. 17, 2012.
International Preliminary Report on Patentability and Written Opinion mailed May 8, 2014 for PCT/US2012/060853 claiming benefit of U.S. Appl. No. 13/653,886, filed Oct. 17, 2012.
International Preliminary Report on Patentability and Written Opinion mailed May 8, 2014 for PCT/US2012/060854 claiming benefit of U.S. Appl. No. 13/653,893, filed Oct. 17, 2012.
International Preliminary Report on Patentability and Written Opinion mailed Nov. 28, 2013 for PCT/US2012/038351 claiming benefit of U.S. Appl. No. 13/111,007, filed May 19, 2011.

(56) References Cited

OTHER PUBLICATIONS

International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability and Written Opinion mailed on Mar. 12, 2015 for PCT/US2013/057097 claiming benefit of U.S. Appl. No. 13/597,478, filed Aug. 29, 2012.
International Preliminary Report on Patentability and Written Opinion mailed on May 14, 2015 for PCT/US2013/067505 claiming benefit of U.S. Appl. No. 13/718,129, filed Dec. 18, 2012.
International Preliminary Report on Patentability and Written Opinion mailed Sep. 7, 2012 for PCT/US2011/026333 claiming benefit of U.S. Appl. No. 12/714,023, filed Feb. 26, 2010.
International Preliminary Report on Patentability for PCT/US2007/013223 mailed Dec. 24, 2008 claiming benefit of U.S. Appl. No. 11/756,057, filed May 31, 2007.
International Preliminary Report on Patentability for PCT/US2010/050701 mailed Apr. 12, 2012 claiming benefit of U.S. Appl. No. 12/571,969, filed Oct. 1, 2009.
International Preliminary Report on Patentability mailed Aug. 25, 2011 for PCT/US2010/024073 filed Feb. 12, 2010, claiming benefit of U.S. Appl. No. 12/371,096, filed Feb. 13, 2009.
International Preliminary Report on Patentability mailed Mar. 31, 2011 for PCT/US2009/056670 claiming benefit of U.S. Appl. No. 12/211,407, filed Sep. 16, 2008.
International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Preliminary Report on Patentability mailed Sep. 6, 2013 for PCT/US2012/026356 claiming benefit of U.S. Appl. No. 13/041,883, filed Mar. 7, 2011.
International Preliminary Report on Patentability Report and Written Opinion mailed Sep. 4, 2014 for PCT/US2013/026875 claiming benefit of U.S. Appl. No. 13/400,652, filed Feb. 21, 2012.
International Search Report and Written Opinion for PCT/US2007/013223 mailed Nov. 26, 2007, claiming benefit of U.S. Appl. No. 11/756,057, filed May 31, 2007.
International Search Report and Written Opinion for PCT/US2009/039507 mailed Jul. 14, 2009, claiming benefit of U.S. Appl. No. 12/103,824.
International Search Report and Written Opinion for PCT/US2009/039507 mailed Jul. 14, 2009, claiming benefit of U.S. Appl. No. 12/103,824, filed Apr. 16, 2008.
International Search Report and Written Opinion for PCT/US2009/056670 mailed Mar. 2, 2010 claiming benefit of U.S. Appl. No. 12/211,407, filed Sep. 16, 2008.
International Search Report and Written Opinion for PCT/US2013/026875 mailed Jun. 7, 2013, claiming benefit of U.S. Appl. No. 13/400,652, filed Feb. 21, 2012.
International Search Report and Written Opinion mailed Apr. 14, 2014 for PCT/US2013/067505 claiming benefit of U.S. Appl. No. 13/718,129, filed Dec. 18, 2012.
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Aug. 9, 2011 for PCT/US2011/026333 claiming benefit of U.S. Appl. No. 12/714,023, filed Feb. 26, 2010.
International Search Report and Written Opinion mailed Aug. 24, 2010 for PCT/US2010/038177 claiming benefit of U.S. Appl. No. 12/483,807, filed Jun. 12, 2009.
International Search Report and Written Opinion mailed Dec. 18, 2012 for PCT/US2012/059189, which claims benefit of U.S. Appl. No. 13/597,478, filed Aug. 29, 2011.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Feb. 6, 2013 for PCT/US2012/060842, which claims benefit of U.S. Appl. No. 13/653,868, filed Oct. 17, 2012.
International Search Report and Written Opinion mailed Feb. 6, 2013 for PCT/US2012/060854, which claims benefit of U.S. Appl. No. 13/653,893, filed Oct. 17, 2012.
International Search Report and Written Opinion mailed Jul. 10, 2014 for PCT/US2014/023655 claiming benefit of U.S. Appl. No. 13/800,369, filed Mar. 13, 2013.
International Search Report and Written Opinion mailed Jul. 31, 2009 for PCT/US2009/039578 claiming benefit of U.S. Appl. No. 12/103,834, filed Apr. 16, 2008.
International Search Report and Written Opinion mailed Jun. 10, 2010 for PCT/US2010/038177 claiming benefit of U.S. Appl. No. 12/483,807, filed Jun. 12, 2009.
International Search Report and Written Opinion mailed Jun. 24, 2014 for PCT/US2014/022000 claiming benefit of U.S. Appl. No. 13/889,869, filed May 8, 2013.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed Mar. 5, 2012 for PCT/US2011/057300 claiming benefit of U.S. Appl. No. 12/938,905, filed Nov. 3, 2010.
International Search Report and Written Opinion mailed May 23, 2014 for PCT/US2013/074288 claiming benefit of U.S. Appl. No. 13/790,770, filed Mar. 8, 2013, which priority is also claimed of U.S. Appl. No. 13/711,306, filed Dec. 11, 2012.
International Search Report and Written Opinion mailed May 8, 2012 for PCT/US2012/026356 claiming benefit of U.S. Appl. No. 13/041,883, filed Mar. 7, 2011.
International Search Report and Written Opinion mailed May 9, 2011 for PCT/US2011/026412 claiming benefit of U.S. Appl. No. 12/872,663, filed Aug. 31, 2010.
International Search Report and Written Opinion mailed Nov. 15, 2012, for PCT/US2012/052853, which claims benefit of U.S. Appl. No. 13/221,968, filed Aug. 31, 2011.
International Search Report and Written Opinion mailed Oct. 14, 2013 for PCT/US2013/057097 claiming benefit of U.S. Appl. No. 13/597,478, filed Aug. 29, 2012.
International Search Report and Written Opinion mailed Oct. 5, 2010 for PCT/US2010/038845 claiming benefit of U.S. Appl. No. 12/486,992, filed Jun. 18, 2009.
International Search Report and Written Opinion mailed on May 8, 2015 for PCT/US2014/068131 claiming benefit of U.S. Appl. No. 13/095,565, filed Dec. 3, 2013.
International Search Report mailed Nov. 30, 2010 for PCT/EP2010/061630 filed Aug. 10, 2010 claiming benefit of DE102009028503.2 filed Aug. 13, 2009.
International Search Report mailed Oct. 23, 2012, for PCT/US2012/041893, which claims benefit of U.S. Appl. No. 61/496,177, filed Jun. 13, 2011.
Invitation to Pay Additional Fees mailed Feb. 6, 2013 for PCT/US2012/060848, which claims benefit of U.S. Appl. No. 13/653,878, filed Oct. 17, 2012.
Invitation to Pay Additional Fees mailed Feb. 6, 2014 for PCT/US2013/067505, which claims benefit of U.S. Appl. No. 13/718,129, filed Dec. 18, 2012.
Invitation to Pay Additional Fees mailed Feb. 7, 2013 for PCT/US2012/060853, which claims benefit of U.S. Appl. No. 13/653,893, filed Oct. 17, 2012.
Invitation to Pay Additional Fees mailed May 3, 2011 for PCT/US2011/026333 claiming benefit of U.S. Appl. No. 12/714,023, filed Feb. 26, 2010.
Invitation to Pay Additional Fees with Partial International Search mailed Nov. 26, 2009 for PCT/US2009/056670.
Japanese Office Action mailed on Apr. 7, 2015 for PCT/US2012/038351 filed May 17, 2012 claiming benefit of U.S. Appl. No. 13/111,007, filed May 19, 2011.

(56) References Cited

OTHER PUBLICATIONS

K. Subburaj et al., "Automated 3D Geometric Reasoning in Computer Assisted Joint Reconstructive Surgery", IEEE International Conference on Automation Science and Engineering, Publication Year: 2009, pp. 367-372.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Patent Examiniation Report No. 1 mailed Feb. 16, 2015 for PCT/US2013/026875 filed Feb. 20, 2013, which claims benefit of U.S. Appl. No. 13/400,652, filed Feb. 21, 2012.

Portheine, F., "CT-basierte Planung und DISOS-Schablonennavigation in der Kniegelenkendoprothetik," in Navigation und Robotic in der Gelenk—und Wirbelsaulenchirugie, Kapitel 32, Springer Verlag (2003) pp. 262-269.

Portheine, F., et al., Entwicklung eines klinischen Demonstrators fur die computerunterstutzte Orthopadische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Gotzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Signature.TM. Personalized Patient Care, Surgical Technique Addendum Vanguard.RTM. Complete Knee System, Biomet.RTM. Orthopedics Brochure, (2011), pp. 1-32.

Signature™ Personalized Patient Care. Surgical Technique Acetabular Guide System brochure. Biomet® Orthopedics. (2013) pp. 1-13.

Sisto, Domenick, J., et al., "Custom Patellofemoral Arthroplasty of the Knee Surgical Technique," Journal of Bone and Joint Surgery, vol. 89-A, pp. 214-225 (Jul. 2006).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

Thomas, W., et al., "Endoprothetischen Versorgung des Kniegelenks auf der Basis eines 3D-computertomographischen Subtraktionsverfahrens," Zuma Thema: Computergestüzte orthopädische Chirugie, Der Orthopäde 29:641-644 Springer-Verlag (Jul. 2000) Translation provided: Thomas, W., "Endoprosthetic care of the knee joint based on a 3D computer chromatography subtraction process," Topic: Computer-aided orthopedic surgery. Orthopedist 2000 29:641-644 Springer Verlag (Jul. 2000).

What is Subchondroplasty, Retrieved from <http://www.subchondroplasty.com/about_subchondroplasty/what_is_subchondroplasty. >, Jul. 1, 2013. 2 sheets.

"U.S. Appl. No. 13/221,968, Advisory Action mailed Sep. 18, 2014", 8 pgs.

"U.S. Appl. No. 13/221,968, Final Office Action mailed Jun. 10, 2014", 16 pgs.

"U.S. Appl. No. 13/221,968, Non Final Office Action mailed Nov. 13, 2013", 21 pgs.

"U.S. Appl. No. 13/221,968, Notice of Allowance mailed Feb. 11, 2015", 7 pgs.

"U.S. Appl. No. 13/221,968, Notice of Allowance mailed Oct. 31, 2014", 5 pgs.

"U.S. Appl. No. 13/221,968, Response filed Feb. 13, 2014 to Non Final Office Action mailed Nov. 13, 2013", 12 pgs.

"U.S. Appl. No. 13/221,968, Response filed Sep. 5, 2014 to Final Office Action mailed Jun. 10, 2014", 11 pgs.

"U.S. Appl. No. 13/221,968, Response filed Sep. 30, 2014 to Advisory Action mailed Sep. 18, 2014", 15 pgs.

"U.S. Appl. No. 13/718,129, Final Office Action mailed Aug. 5, 2015", 17 pgs.

"U.S. Appl. No. 13/718,129, Non Final Office Action mailed Feb. 5, 2015", 19 pgs.

"U.S. Appl. No. 13/718,129, Notice of Allowance mailed Nov. 18, 2015", 10 pgs.

"U.S. Appl. No. 13/718,129, Response filed Jan. 20, 2015 to Restriction Requirement mailed Nov. 19, 2014", 1 pg.

"U.S. Appl. No. 13/718,129, Response filed Jun. 5, 2015 to Non Final Office Action mailed Feb. 5, 2015", 14 pgs.

"U.S. Appl. No. 13/718,129, Response filed Nov. 3, 2015 to Final Office Action mailed Aug. 5, 2015", 14 pgs.

"U.S. Appl. No. 13/718,129, Restriction Requirement mailed Nov. 19, 2014", 6 pgs.

(56) References Cited

OTHER PUBLICATIONS

"Biomet Orthopedics", Brochure E-POL Y HSLPE (EXH20), (2007), 23 pgs.

"Japanese Application Serial No. 2014511538, Office Action mailed Apr. 7, 2015", (W/ English Translation), 8 pgs.

"MAX-Ti™ Modular Protrusio Cage", Surgical Technique brochure. Biomet Orthopedics, Inc., (2003), 10 pgs.

"Signature™ Hip Technology Personalized Patient Care brochure", Biomet® Orthopedics., (2013), 8 pgs.

"United Kingdom Application Serial No. 1405068.6, Office Action mailed May 27, 2014", 2 pgs.

* cited by examiner

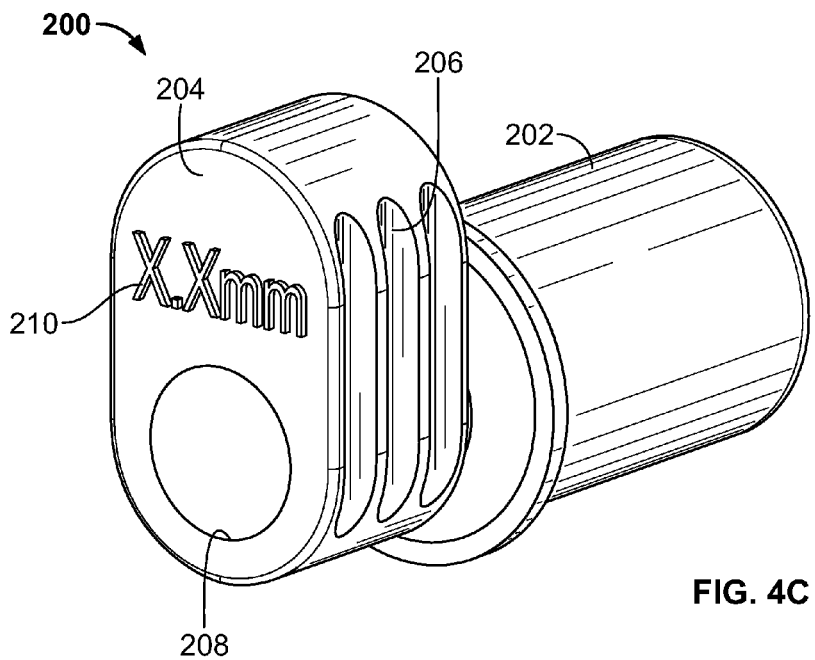
FIG. 4C
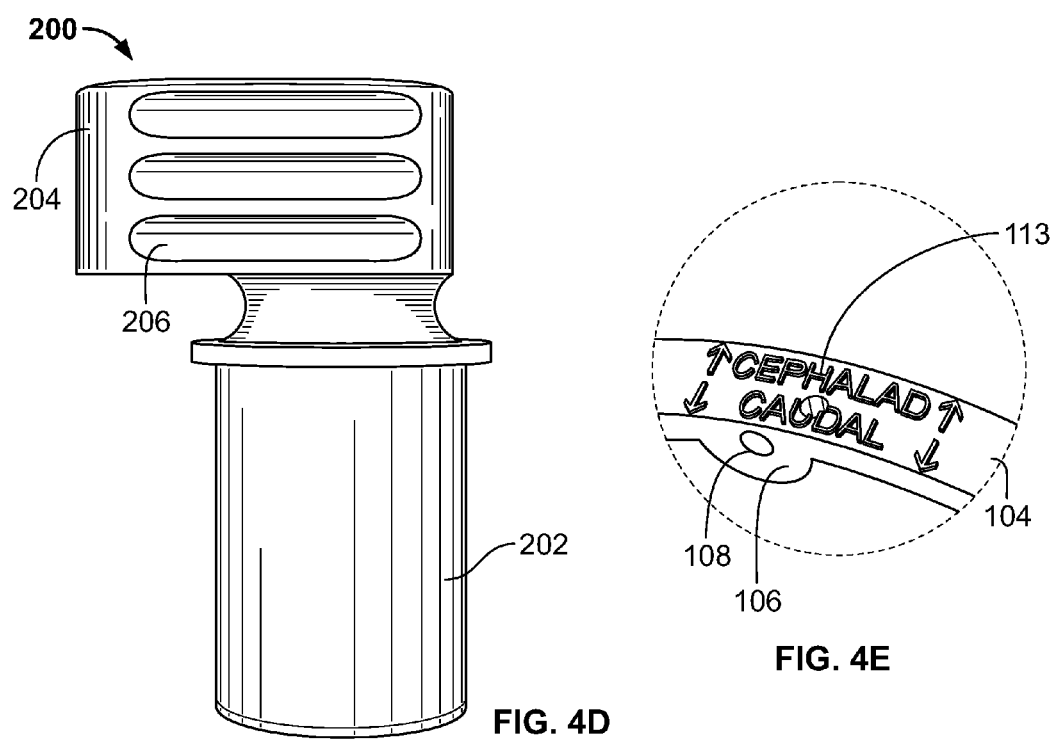
FIG. 4D
FIG. 4E

PATIENT-SPECIFIC SACROILIAC GUIDES AND ASSOCIATED METHODS

CROSS-REFERENCE TO RELATED APPLICATIONS

This application is a continuation of U.S. patent application Ser. No. 13/221,968 filed on Aug. 31, 2011. The entire disclosure of the above application is incorporated herein by reference.

FIELD AND INTRODUCTION

The present teachings provide various patient-specific alignment guides for sacro-pelvic, sacroiliac and/or posterior iliac fixation. The patient-specific alignment guides facilitate more accurate placement of bone screws and other fixation devices that are used in various spinal fixation systems, such as, for example, thoracic and lumbar rod systems. The patient-specific alignment guides are designed and constructed preoperatively based on three-dimensional digital images of portions of the patient's pelvis and spine, including the ilium and the sacrum. The digital images of the patient's anatomy can be reconstructed from medical scans of the patient using commercially available CAD (Computer Aided Design) and/or other imaging software.

SUMMARY

The present teachings provide orthopedic devices that include patient-specific alignment guides for various lumbopelvic fixation procedures. In some embodiments, the patient-specific alignment guide can be preoperatively configured for unilateral fixation, bilateral fixation, sacral fixation and/or sacroiliac fixation and combinations thereof. In some embodiments, the patient-specific alignment guide can be modular and intraoperatively convertible and reconfigurable at the discretion of the operating surgeon.

In some embodiments, the patient-specific alignment guide includes a patient-specific portion and a guiding element having a through opening. The patient-specific portion has a patient-specific surface preoperatively configured to nestingly mate as a negative of a portion of an iliac crest of a pelvis of a specific patient and mate to the iliac crest only in one position. The guiding element has a preoperatively configured orientation and location relative to the patient-specific portion for preparing a bore in the bone of the patient to direct a bone screw at the preoperatively configured orientation and location for sacroiliac fixation.

In some embodiments, the patient-specific alignment guide includes first and second patient-specific portions coupled by an arcuate bridge. The first patient-specific portion has a patient-specific surface preoperatively configured to nestingly mate to a portion of a first iliac crest of a pelvis of a specific patient and mate to the first iliac crest only in one position. The second patient-specific portion is similarly constructed for a second iliac crest of the patient. The bridge is configured to span a posterior contour of the pelvis of the patient. The patient-specific alignment guide can include first and second iliac guiding elements coupled to the corresponding first and second patient-specific portions, and first and second sacral guiding elements coupled to the bridge. Each of the first and second iliac and sacral guiding elements has a through opening and a preoperatively configured orientation and location relative to one of the first and second patient-specific portions for preparing a corresponding bore in the bone of the patient to direct a corresponding bone screw for sacroiliac fixation.

The present teachings also provide a method for lumbopelvic fixation. The method includes providing a convertible patient-specific alignment guide for a patient's pelvis and intraoperatively selecting one of unilateral fixation, iliac fixation, sacral fixation and bilateral sacroiliac fixation procedure for the patient. The convertible patient-specific alignment guide is reconfigured intraoperatively to a corresponding patient-specific alignment guide for the selected procedure. The convertible patient-specific alignment guide includes first and second patient-specific portions coupled by a bridge.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The drawings described herein are for illustrative purposes only of selected embodiments and not all possible implementations, and are not intended to limit the scope of the present disclosure.

FIG. 4C is a perspective view of a drill guide according to the present teachings;

FIG. 4D is a side view of the drill guide of FIG. 4C;

FIG. 4E is a detail of the patient-specific universal alignment guide of FIG. 4 showing an exemplary marking;

Corresponding reference numerals indicate corresponding parts throughout the several views of the drawings.

DESCRIPTION OF VARIOUS ASPECTS

Figure 1:
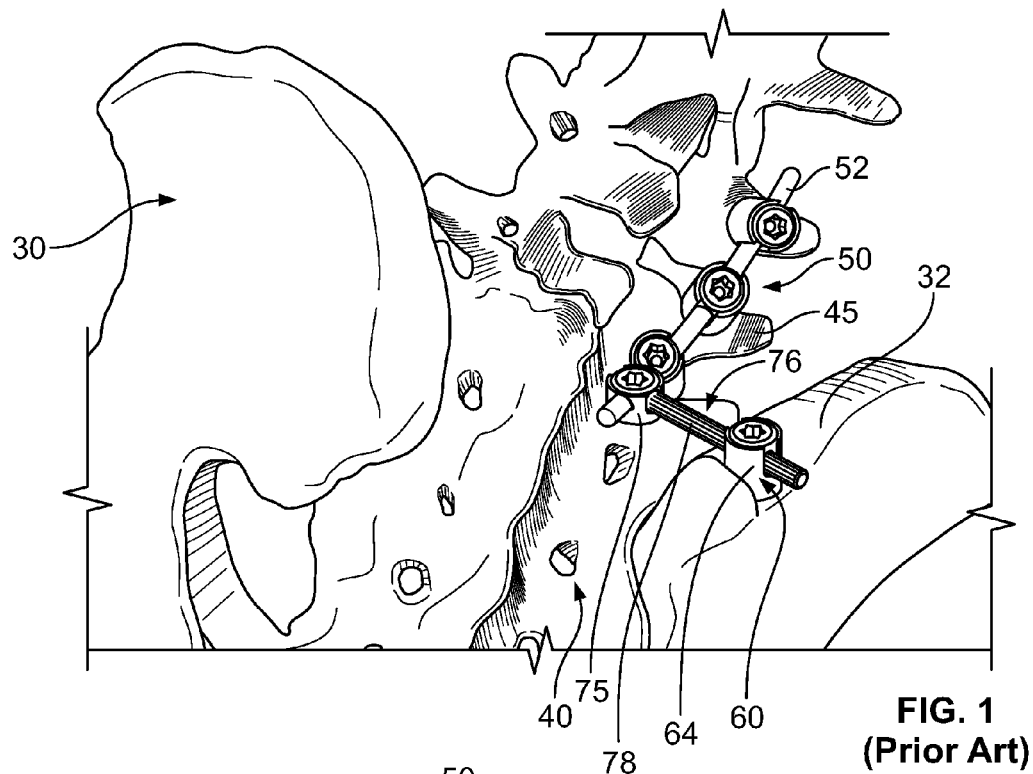
FIG. 1 is an environmental view of a portion of a spinal rod system.

The following description is merely exemplary in nature and is in no way intended to limit the present teachings, applications, or uses. For example, although some of the present teachings are illustrated for sacroiliac fixation, the present teachings can be used for any other lumbopelvic procedure or lumbar and/or pelvic correction including trauma, deformation or disease.

The present teachings provide various patient-specific alignment guides for sacro-pelvic, sacroiliac and/or posterior iliac fixation. The patient-specific alignment guides can facilitate and improve the accuracy of the placement of bone screws and other fixation devices that are used in various spinal fixation systems, such as, for example, thoracic, lumbar and lumbopelvic fixation systems.

The patient-specific alignment guides of the present teachings are designed to guide and facilitate lumbopelvic fixation and help mitigate bone screw breaches of bone or neurovascular injury that can sometimes happen during unguided implantation of a lumbopelvic fixation system. Further, unguided implantation can be complicated by the characteristic three-dimensional geometry of the sacroiliac anatomy and/or the difficulty in directing bone screws toward strong bone anchorage, especially in the presence of cortical deficiencies, such as those that can be caused by previous autograft harvest from the posterior superior iliac spine (PSIS). Additionally, the receiver element of a bone screw assembly that is configured to receive a rod of a lumbopelvic fixation system and also support a corresponding bone screw can further complicate the placement of the bone screws connected to the corresponding receiver elements. The patient-specific alignment guides of the present teachings are preoperatively configured to alleviate or reduce some of these complications for each specific patient.

The patient-specific alignment guides are designed and constructed preoperatively based on three-dimensional digital images of portions of the patient's pelvis and spine, including the ilium, iliac wings and iliac crests and the sacrum. The three-dimensional digital images of the patient's anatomy can be reconstructed preoperatively from MRI, CT, ultrasound, X-ray, or other imaging and medical scans of the patient's anatomy using computer-assisted image methods. Various CAD programs and/or software can be utilized for three-dimensional image reconstruction, such as, for example, software commercially available by Materialise USA, Plymouth, Mich.

Various pre-operative planning procedures and patient-specific alignment guides are described in commonly assigned and co-pending U.S. patent application Ser. No. 11/756,057, filed May 31, 2007, now U.S. Patent Publication No. 2007/0288030; U.S. patent application Ser. No. 12/025,414, filed Feb. 4, 2008, now U.S. Patent Publication No. 2008/0114370; U.S. patent application Ser. No. 12/103,824, filed Apr. 16, 2008, now U.S. Patent Publication No. 2008/0257363; U.S. patent application Ser. No. 12/371,096, filed Feb. 13, 2009, now U.S. Patent Publication No. 2009/0151736; U.S. patent application Ser. No. 12/483,807, filed Jun. 12, 2009, now U.S. Patent Publication No. 2009/0254367; U.S. patent application Ser. No. 12/872,663, filed Aug. 31, 2010, now U.S. Patent Publication No. 2010/0324692; U.S. patent application Ser. No. 12/973,214, filed Dec. 20, 2010, now U.S. Patent Publication No. 2011/0092804; and, U.S. patent application Ser. No. 12/978,069, filed Dec. 23, 2010, now U.S. Patent Publication No. 2011/0093086. The disclosures of the above applications are incorporated herein by reference.

In the preoperative planning stage for lumbopelvic fixation, a preoperative surgical plan is formulated for a specific patient with interactive input from the patient's surgeon or other medical professional. Imaging data of the relevant anatomy of a patient can be obtained at a medical facility or doctor's office, using any of the medical imaging methods described above. The imaging data can include, for example, various medical scans of a relevant joint portion or other relevant portion of the patient's anatomy, as needed for the particular surgical procedure. The imaging data thus obtained and other associated information can be used to construct a three-dimensional computer (digital) image of a relevant portion of the anatomy of the patient, such as, in the present application, portions of the patient's pelvis and spine, including the sacral and iliac regions. The three-dimensional digital image of the patient's anatomy can be used to formulate a preoperative surgical plan specific to the patient. The preoperative surgical plan can include the design and construction of implants, patient-specific alignment guides and other instruments according to selected methods of surgical preparation and implantation. The preoperative surgical plan can also include planning for the location and orientation of bone modifications and/or resections and trajectory paths for various implant components, including, for example bone screws.

Generally, the patient-specific alignment guides of the present teachings are configured to match portions of the iliac and/or sacral anatomy of a specific patient and are generally designed and configured using computer modeling based on the reconstructed three-dimensional digital image of the patient's corresponding anatomy, as discussed above. The patient-specific alignment guides have a patient-specific anatomy-engaging surface that is configured as a mirror or negative or complementary surface that can conformingly contact and match a corresponding bone surface of the patient (with or without cartilage or other soft tissue). In this respect, a patient-specific alignment guide can register to and nestingly mate with the corresponding bone surface, such as, for example, a portion of the iliac crest, of the specific patient in only one position. The patient-specific alignment guides of the present teachings can be configured for use in any surgical procedure, such as open, mini-open and minimally invasive procedure.

The three-dimensional model of the patient's anatomy can be viewed on a computer display or other electronic screen and can also be reproduced as a hard copy on film or other medium and viewed by direct or indirect or backlight illumination. The model can be sized for viewing on any appropriate screen size and may be cropped, rotated, etc., as selected by the individual (e.g., the surgeon) viewing the screen.

The patient-specific alignment guides can be manufactured by rapid prototyping methods, such as stereolithography or other similar methods, or by CNC milling, or other automated or computer-controlled machining or robotic methods. The patient-specific alignment guides can be manufactured from any biocompatible materials, including metals, polymers and combinations thereof. The patient-specific alignment guides, the implants for the surgical procedure and, optionally, other disposable instruments can be sterilized, packaged and forwarded to the surgeon or the surgeon's medical facility for the surgical procedure.

Figure 2:
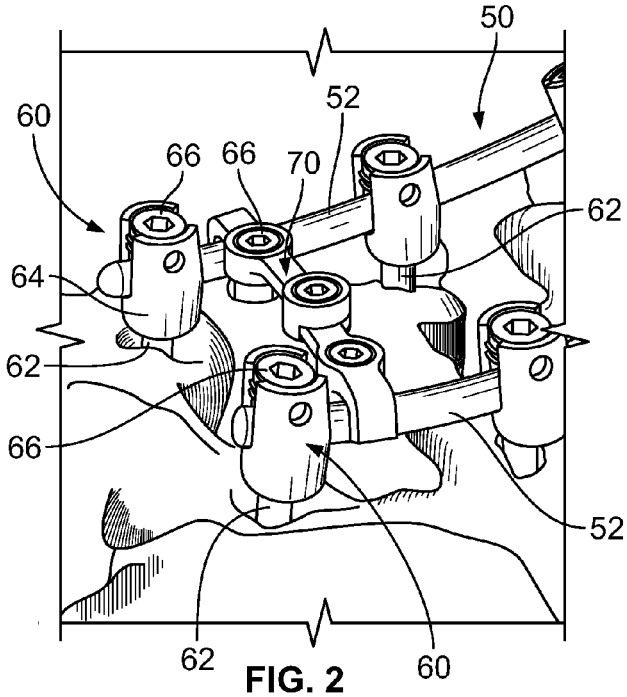
FIG. 2 is an environmental view of a portion of another spinal rod system.
Figure 3:
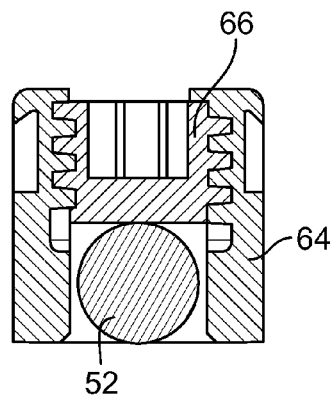
FIG. 3 is a detail of a multi-axial screw assembly of the spinal rod system shown in FIG. 2.
Figure 4:
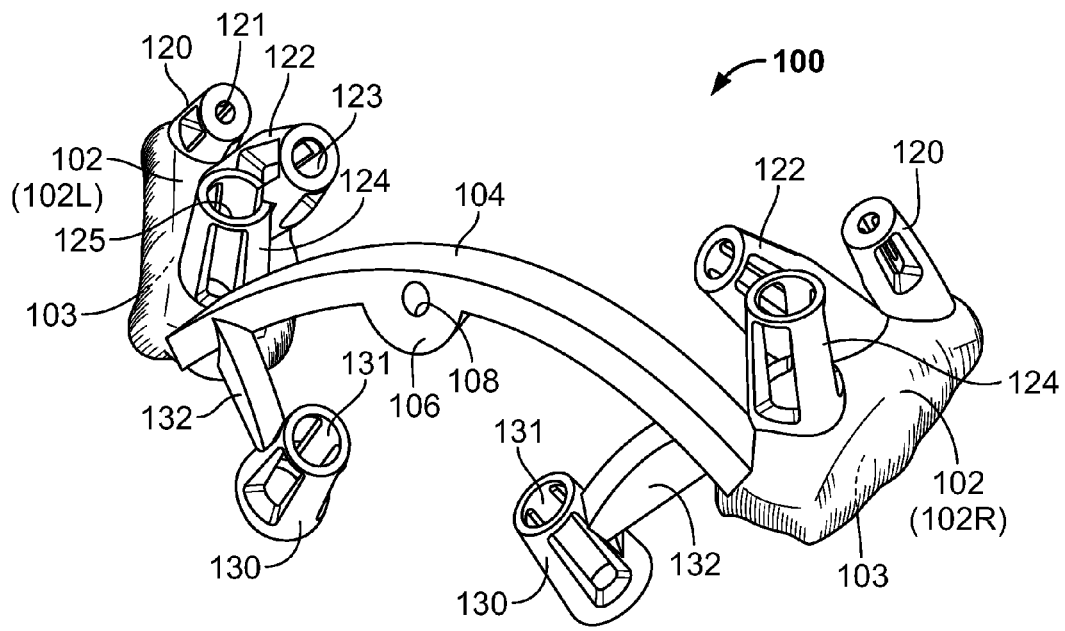
FIG. 4 is a perspective view of a patient-specific universal alignment guide according to the present teachings.
Figure 5:
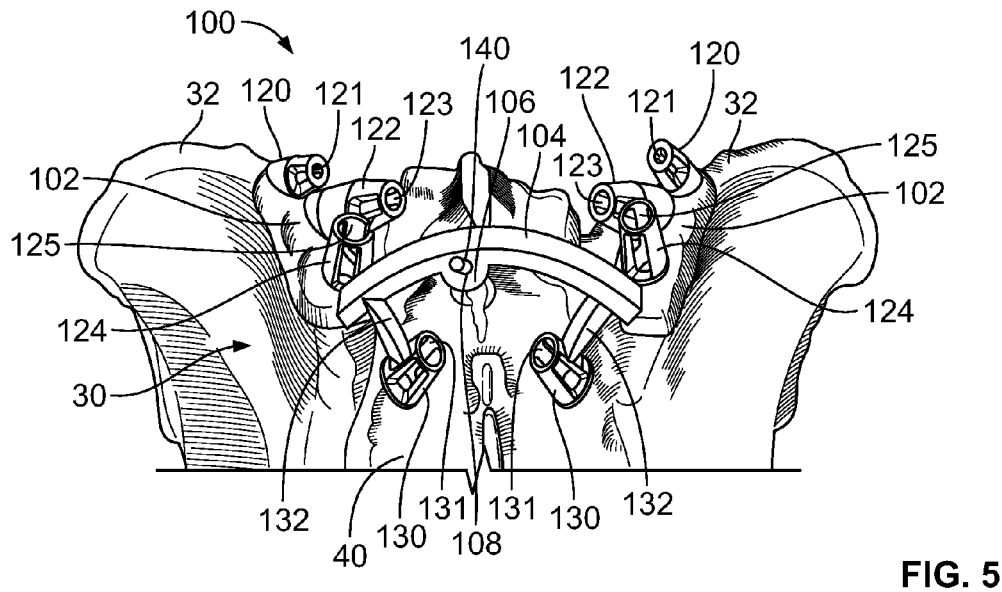
FIG. 5 is an environmental view of the universal alignment guide of FIG. 4.
Figure 5A:
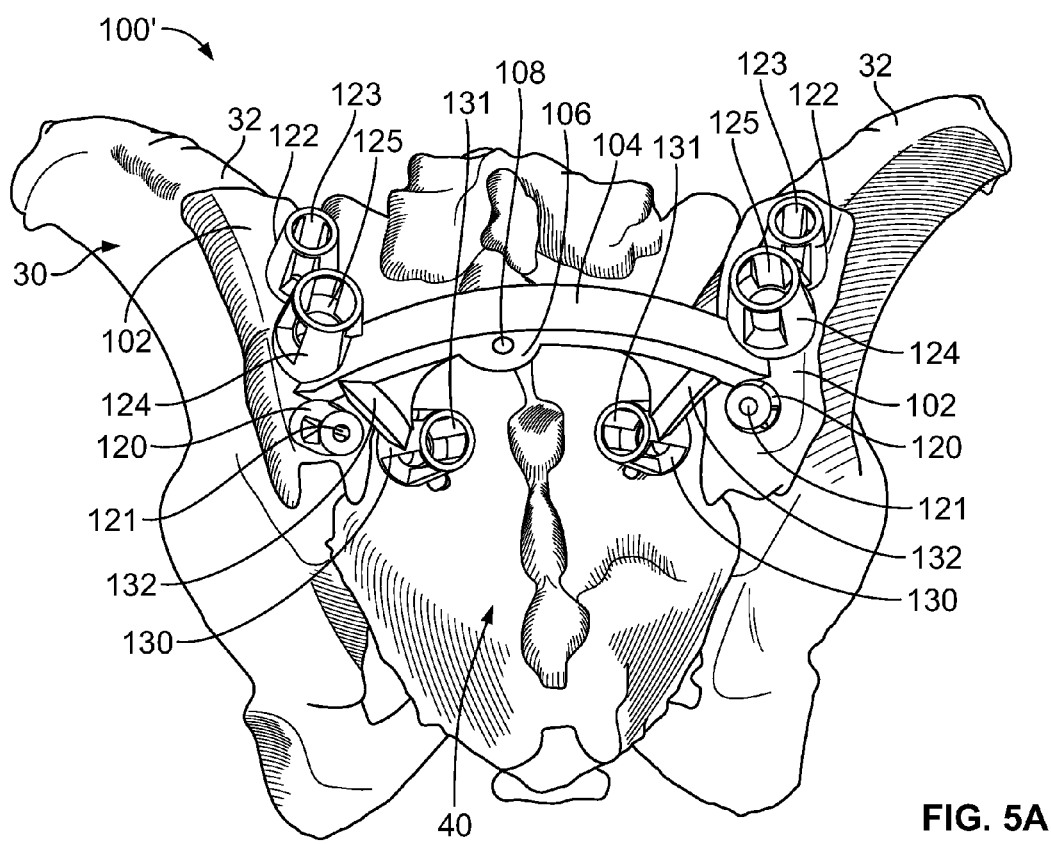
FIG. 5A is an environmental view of another universal alignment guide according to the present teachings.
Figure 6:
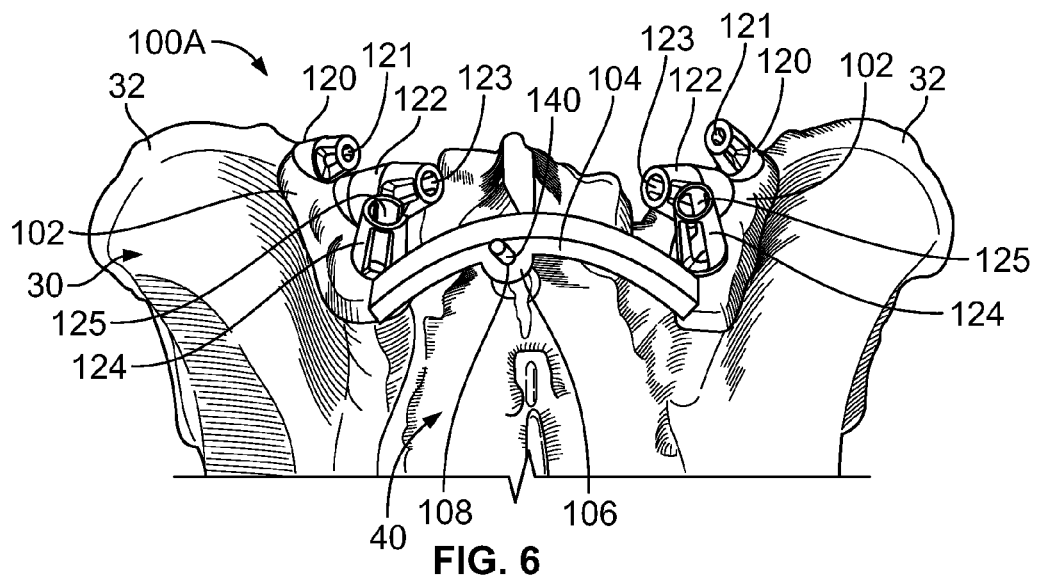
FIG. 6 is an environmental view of a patient-specific iliac alignment guide according to the present teachings.
Figure 7:
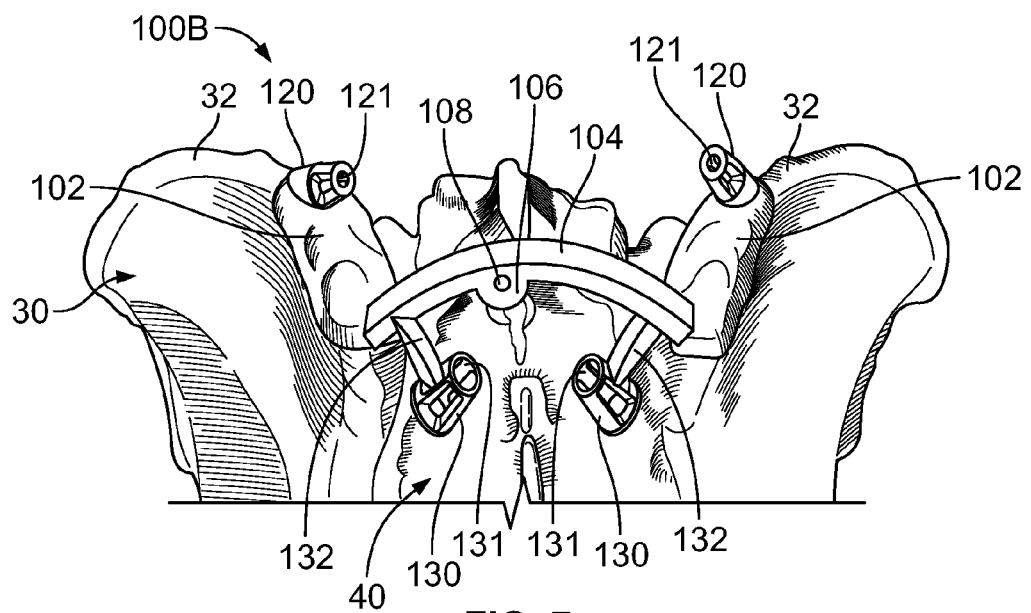
FIG. 7 is an environmental view of a patient-specific sacral alignment guide according to the present teachings.
Figure 8:
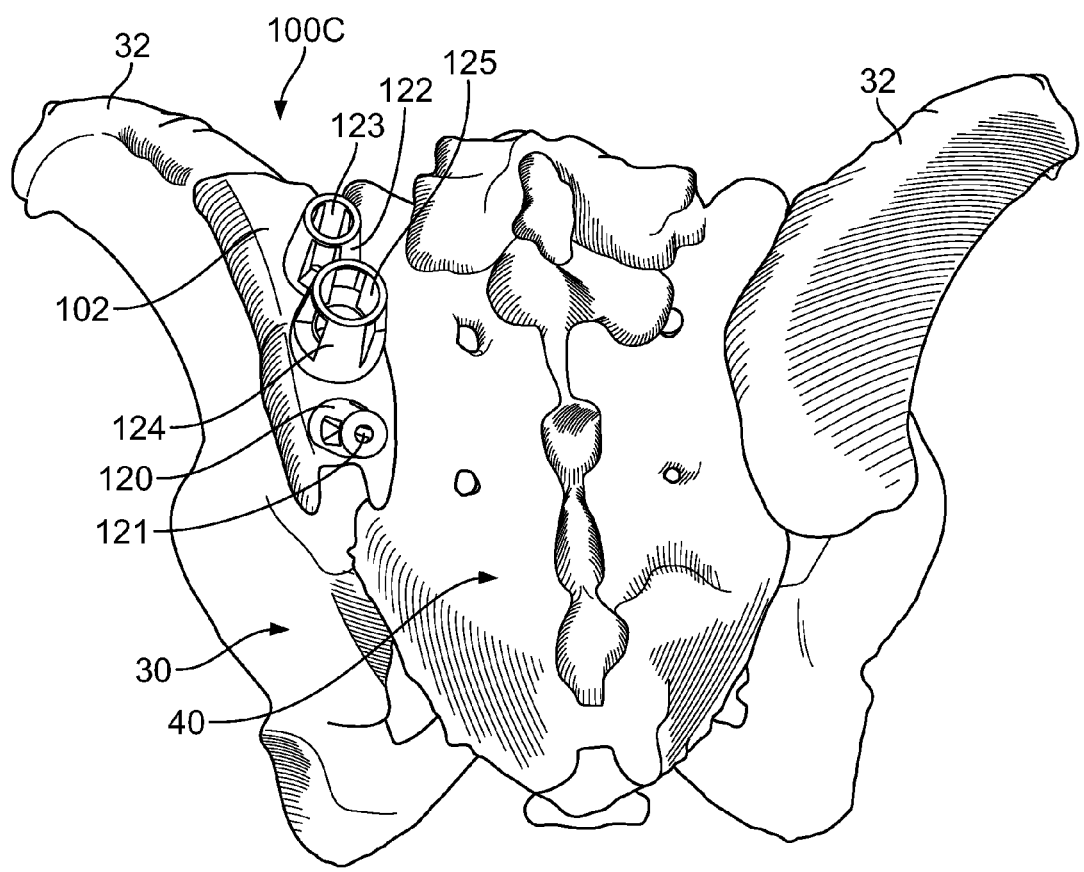
FIG. 8 is an environmental view of a unilateral iliac alignment guide according to the present teachings.
Figure 9:
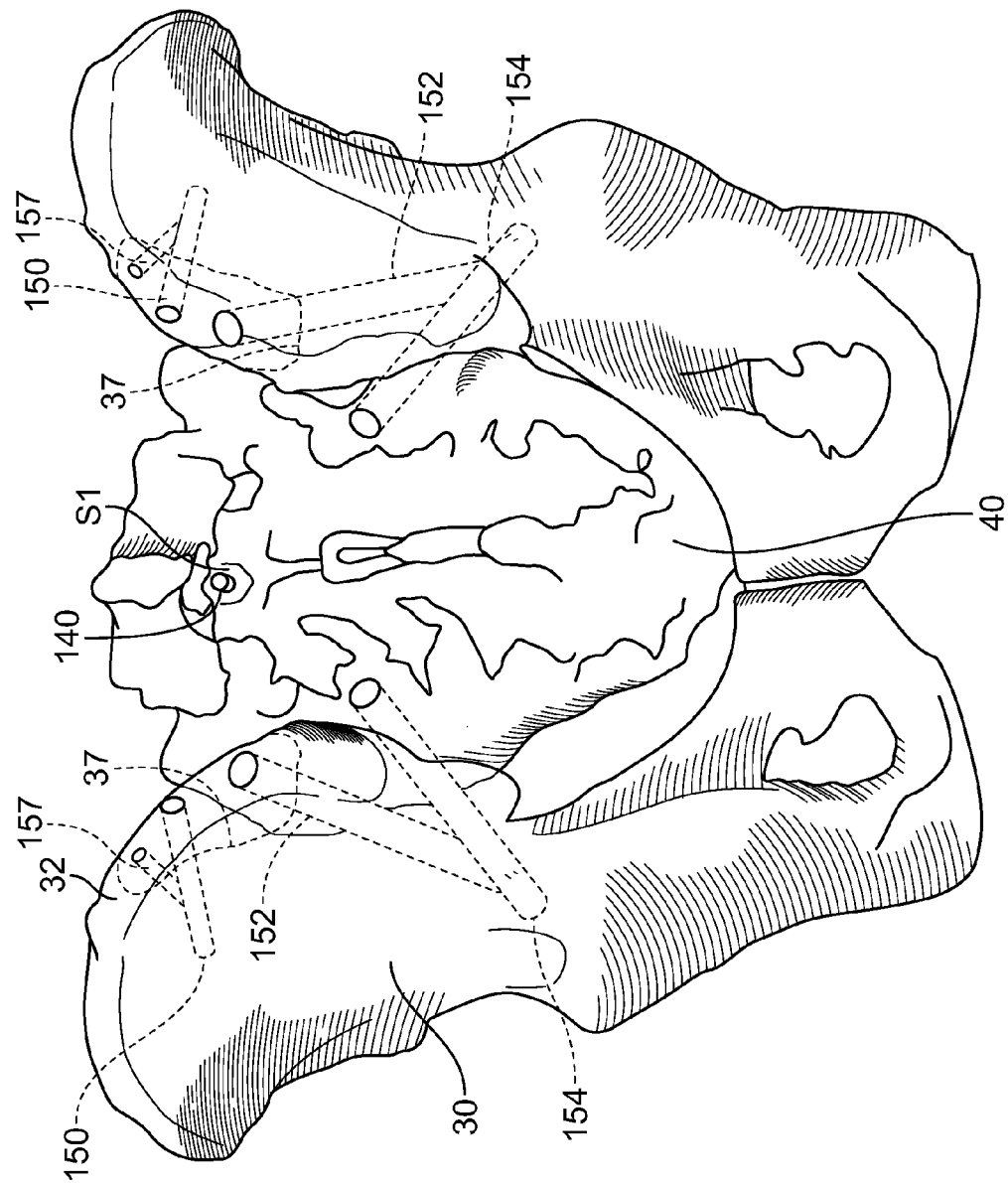
FIG. 9 is an environmental view of a patient's pelvis showing representative bores drilled into the pelvis using the patient-specific alignment guides of FIG. 5, 5A, 7 or 8.

As a brief overview, and referring to FIGS. 1-13, prior art spinal fixation systems are briefly described in reference to FIGS. 1-3. Various embodiments of patient-specific alignment guides are described in reference to FIGS. 4-8. For example, FIG. 6 illustrates a patient-specific "iliac" guide 100A for inserting fixation screws starting from and into the ilium of the patient, according to the present teachings. FIG. 7 illustrates a patient-specific "sacral" guide 100B for inserting fixation screws from the sacrum and into the ilium, according to the present teachings. FIGS. 4, 5 and 5A illustrate "universal" patient-specific guides 100, 100' for inserting bilaterally or unilaterally fixation screws from and into the ilium and/or from the sacrum and into the ilium according to the present teachings. FIG. 8 illustrates a patient-specific unilateral iliac guide 100C for inserting fixation screws into the left ilium according to the present teachings. FIG. 9 illustrates screw bores prepared in the bone using an alignment guide of the present teachings and shown after the alignment guide is removed. Post implantation details of the lumbopelvic fixation system implanted using the bores pre-drilled with the alignment guides of the present teachings are shown in FIGS. 8-13.

Referring to FIGS. 1-3, portions of prior art spinal fixation systems (or rod systems) are illustrated. Various spinal and/or lumbopelvic fixation systems are commercially available from Biomet Manufacturing Corp., Warsaw, Ind., and include, for example, the Polaris® fixation system and the Array® fixation system. An exemplary spinal fixation system 50 can include elongated fixation members or rods 52 that can be attached to the patient's anatomy with bone screw assemblies 60 inserted into thoracic pedicles, lumbar pedicles 45, sacrum 40 and/or iliac wings 30 or iliac crest 32 of a patient's pelvis depending on the surgical technique and the corrective procedure selected for the patient. The bone screw assembly 60 can include a bone screw 62 with a bone anchoring portion inserted into the bone, a U-shaped ("tulip") receiver 64, and a securing cap 66. The receiver 64 is configured to receive or support the head of the bone screw 62 and optionally allow multi-axial pivoting of the bone screw 62. The receiver 64 is also configured to transversely hold the rod 52. The securing cap 66 is received and/or engaged to the receiver 64 and locks the rod 52 and the bone screw 62. In other embodiments, the bone screw assembly 60 can include fixed, rather than polyaxial, bone screws.

With continued reference to FIGS. 1-3, cross-connectors 70 between two rods 52 can be used to provide additional stability to the spinal fixation system 50 along the spine. Further, lateral connectors 76 can be used to provide iliac fixation and extend the spinal fixation system 50 over the iliac wings, as shown in FIG. 1. The lateral connector 76 shown in FIG. 1 includes, for example, a receiver portion 75 coupled to the rod 52 and an elongated shaft 78 coupled to a bone screw assembly 60 that is positioned through the iliac crest 32. Exemplary embodiments of the spinal fixation system 50 and associated instruments and implants, including the bone screw assembly 60 with the optional cross connectors 70 and lateral connectors 76 are commercially available from Biomet Manufacturing Corp., Warsaw, Ind. It will be appreciated, however, that other spinal fixation systems can be used according to the present teachings including, for example, the spinal fixation systems, bone screw assemblies, cross connectors and lateral connectors described in U.S. Pat. Nos. 7,294,129, 6,302,888, 6,616,668 and 7,699,876, the disclosures of which are incorporated herein by reference.

Figure 4A:
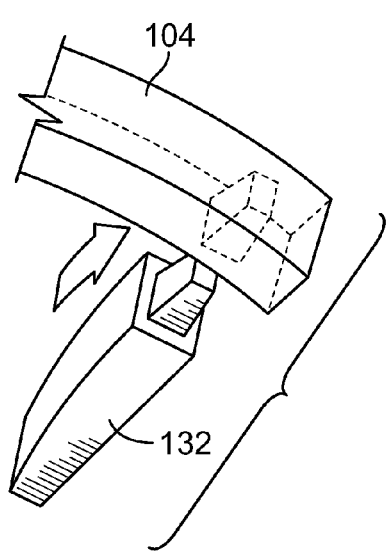
FIG. 4A is a detail of another embodiment of the patient-specific universal alignment guide of FIG. 4.

Referring to FIGS. 4-5A, 9 and 10, two embodiments of a universal patient-specific sacroiliac alignment guide 100, 100' ("the universal guide" for short) are illustrated. The universal guide 100, 100' is preoperatively configured to guide the drilling of one or more "iliac" (starting at the iliac wing or iliac crest) bores 150, 152 and one or more "sacral" (starting at the sacrum) bores 154 (see FIG. 9) to implant corresponding iliac and sacral bone screws 61, 63, 65 for a spinal fixation system 50 (see FIG. 10). As can be seen in FIG. 9, the iliac bores 150, 152 are initiated from an iliac crest 32 and are directed into an iliac wing 30. The sacral bores 154 initiated from the sacrum 40 and are also directed into the iliac wing 30 through a corresponding sacroiliac joint. The two embodiments of the universal guide 100, 100' have many similar elements and will be commonly described, except as noted to highlight any differences. Each universal guide 100, 100' can include first and second patient-specific portions 102 (right 102R, left 102L) that can be either integrally (monolithically) or modularly (removably) connected to one another by an elongated curved or arcuate connector or bridge 104. The bridge 104 can include a tab portion 106 with a through hole 108 for receiving a locating pin 140 (K-wire or other type of pin) referencing the first sacral process (S1) of the spine, as shown in FIGS. 5 and 9. The locating pin 140 can be used to confirm the accurate placement of the universal guide 100, 100' by intraoperatively trialed to confirm contact with the S1 sacral process. The locating pin 140 can also be used for other anatomic landmarks, such as one or more sacral or spinous processes. The arcuate shape of the bridge 104 generally follows the contour of the posterior surface of the pelvis and can facilitate an effortless placement of the universal guide 100, 100' on the specified anatomy. The bridge 104 can also function as a handle for holding or guiding the universal guide 100, 100' on the pelvis. The bridge 104 can be removably coupled to each patient-specific portion 102 by a taper-to-taper or other releasable connection, as shown in the exemplary illustration of FIG. 4A.

With continued reference to FIGS. 4-5A, 9 and 10, each patient-specific portion 102 is preoperatively configured from a three-dimensional image of the pelvis of the patient that is reconstructed from medical scans of the patient, as discussed above. Specifically, the patient-specific portion 102 has a patient-specific surface 103 configured as a negative or mirror of a portion of the iliac crest 32 and, optionally, adjacent areas. The patient-specific surface 103 tracks the unique anatomy of the specific patient's iliac crest 32 that provides natural referencing landmarks. Accordingly, the patient-specific portion 102 can be positioned intraoperatively with accuracy, and without our intraoperative guidance, in a preoperative determined single location of the iliac crest 32. The patient-specific portion 102 nests and nestingly mates to the corresponding iliac crest 32, as shown in FIGS. 5 and 5A. In some embodiments, the patient-specific portion 102 can snap onto the corresponding iliac crest 32.

Each patient-specific portion 102 includes one or more "iliac" guiding elements 122, 124 with corresponding openings 123, 125 passing through the patient-specific portion 102 for guiding a drill or other cutting instrument and forming corresponding iliac bores 150, 152 from the iliac crest 32 through the iliac wing 30. The iliac guiding elements 122, 124 are configured preoperatively with patient-specific orientations and locations. The openings 123, 125 of the iliac guiding elements 122, 124 can be tapered and sized to receive a drill bit either directly or indirectly by receiving a sleeve or other drill guide to stabilize and guide a drill. In other embodiments, the openings 123, 125 can be cylindrical to limit space requirements. In some embodiments, a metal sleeve may be press-fitted into a corresponding opening 123, 125 to provide additional rigidity and stability, especially when the universal guide 100, 100' (or any of the patient-specific alignment guides) is made of polymer or other plastic.

In some embodiments, a drill guide can be used to guide a drill, such as the drill guide 200 shown in FIGS. 4C and 4D. The drill guide 200 can have a space-saving cylindrical shaft 202 with a cylindrical bore 208 and can be configured to be received into a corresponding opening 123, 125 of a corresponding iliac element 122, 124. Each drill guide 200 can be marked with color-coded and/or raised or embossed marking (e.g., X.X mm) indicating the size of the corresponding guiding element 122, 124 with which it can be used. The marking 210 can be placed on an outer surface of a block element 204 that is connected to the shaft 202. The block element 204 can be used as a handle and can include grooves 206 or other tactile or frictional formations for facilitating secure hand gripping. The block element 204 can be offset relative to the shaft 202 in a direction that avoids interfering with visualization during the surgical procedure.

Similarly, the guiding elements 122, 124 can be identified with color-coding and/or raised markings indicating size. Embossed or raised markings 113 can also be provided on the bridge 104 to indicate caudal and cephalad directions for the placement of the universal guide 100, 100' (and the other patient-specific alignment guides of the present teachings).

Figure 4B:
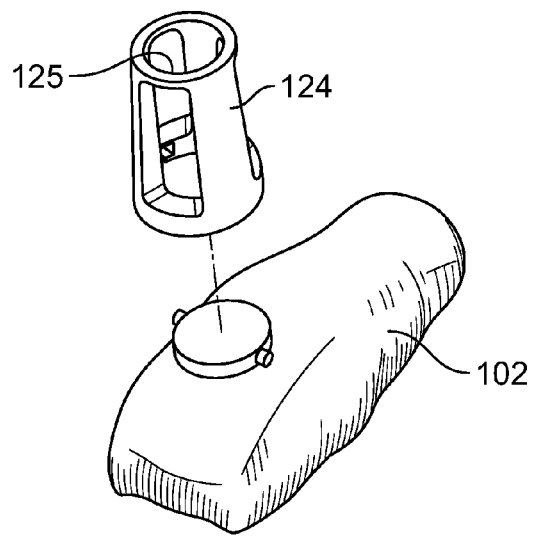
FIG. 4B is a detail of another embodiment of the patient-specific universal alignment guide of FIG. 4.
Figure 10:
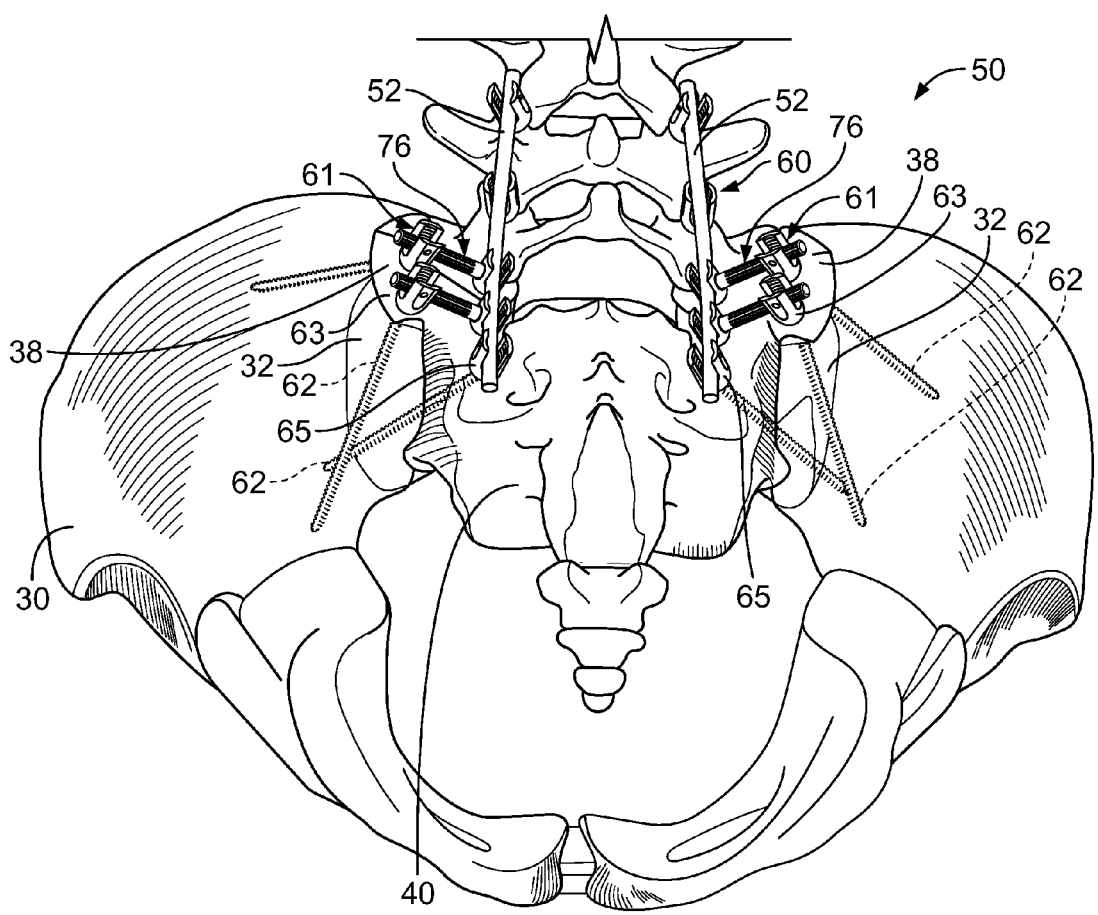
FIG. 10 is an environmental view of a spinal rod system showing sacral and iliac screws positioned with patient-specific alignment guides according to the present teachings.

With continued reference to FIGS. 4-5A, 9 and 10, the universal guide 100, 100' can include one or more elongated arms 132 extending from the bridge 104 toward the sacrum 40 (left and right arms 132 are illustrated). In some embodiments, the arm 104 can extend from the patient-specific portion 102, rather than from the bridge 104. In some embodiments, the arm 132 can be removably coupled to the patient-specific portion 102 or the bridge 104 by a quick-connect/disconnect coupling, such as snap-fit, tongue and groove, taper-to-taper, etc., as shown in an exemplary illustration of FIG. 4A. Each arm 132 can support one (or more) sacral guiding elements 130 having corresponding openings 131. The arm 132 can be curved and oriented such that the sacral guiding element 130 is positioned in a preoperatively determined position and orientation for the specific patient based on the preoperative plan for the patient. The opening 131 of the sacral guiding element 130 can be tapered and sized to receive a drill bit or a sleeve (not shown) for stabilizing and guiding a drill. The sacral guiding element 130 is configured preoperatively with patient-specific orientation and location for guiding a sacral bone screw 65 through a bore 154 drilled from the sacrum 40 into the iliac wing 30 of the patient, as shown in FIGS. 9 and 10. Additionally, the orientations and positions of the iliac guiding elements 122, 124 and sacral guiding elements 130 are configured to avoid interference among the trajectories of the corresponding bone screws and provide anchoring in non-deficient cortical bone. In some embodiments, placement of the bone screws at patient-specific distances from the sciatic notch is preoperatively configured by the arrangement of the iliac and sacral guiding elements 122, 124, 130. Further, in some embodiments, all or some of the iliac and/or sacral guiding elements 122, 124, 130 can be modular or removable and couplable to the corresponding patient-specific portions 102 with taper-to-taper connections, bayonet connections, threadable connections, snap-fit connections or other removable or releasable connections, as illustrated in FIG. 4B. The iliac sacral guiding elements 122, 124, 130 can be color-coded and marked for size with raised or embossed markings, as discussed above.

Figure 6A:
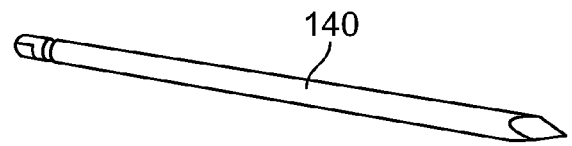
FIG. 6A is a perspective view of a fixation pin shown in FIG. 6.

Each of the patient-specific portions 102 can also include a fixation guiding element 120 with a corresponding opening 121 for guiding a temporary fixation guiding element such as a trocar pin or the pin 140 shown in FIG. 6A for temporarily attaching the universal guide 100, 100' on the pelvis of the patient. The opening 121 of the fixation guiding element 120 can be smaller in diameter than the openings 123, 125 and 131 of the corresponding iliac and sacral guiding elements 122, 124 and 130 that are used for drilling bores for the bone screws 62 of the iliac and sacral screw assemblies, as shown in FIG. 9. The fixation guiding element 120 is shown as located cephaladly (superiorly) on the patient-specific portion 102 of the universal guide 100 in FIGS. 4 and 5, and caudally (inferiorly) on the patient-specific portion 102 of the universal guide 100' shown in FIG. 5A. In some embodiments, the patient-specific portion 102 of the universal guide 100' can extend further caudally along the iliac crest 32, and the bridge 104 of the universal guide 100' can extend from a position cephalad to the fixation guiding element 120, as shown in FIG. 5A. The locations of the temporary fixation pins 140 that are used to support the universal alignment guide 100 on the pelvis are shown at 157 in FIG. 9.

Figure 11:
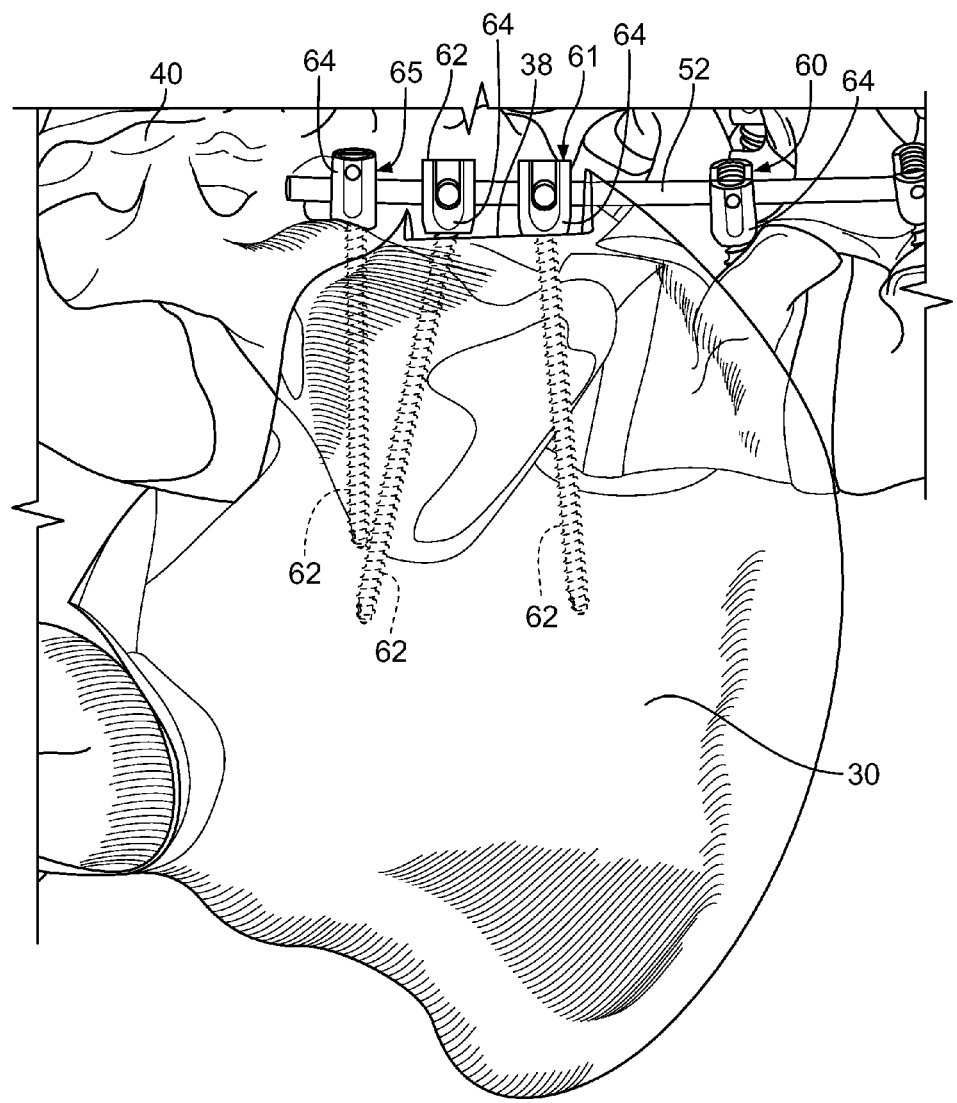
FIGS. 11-13 are different environmental perspective views showing placement of sacral and iliac screws according to the present teachings.
Figure 12:
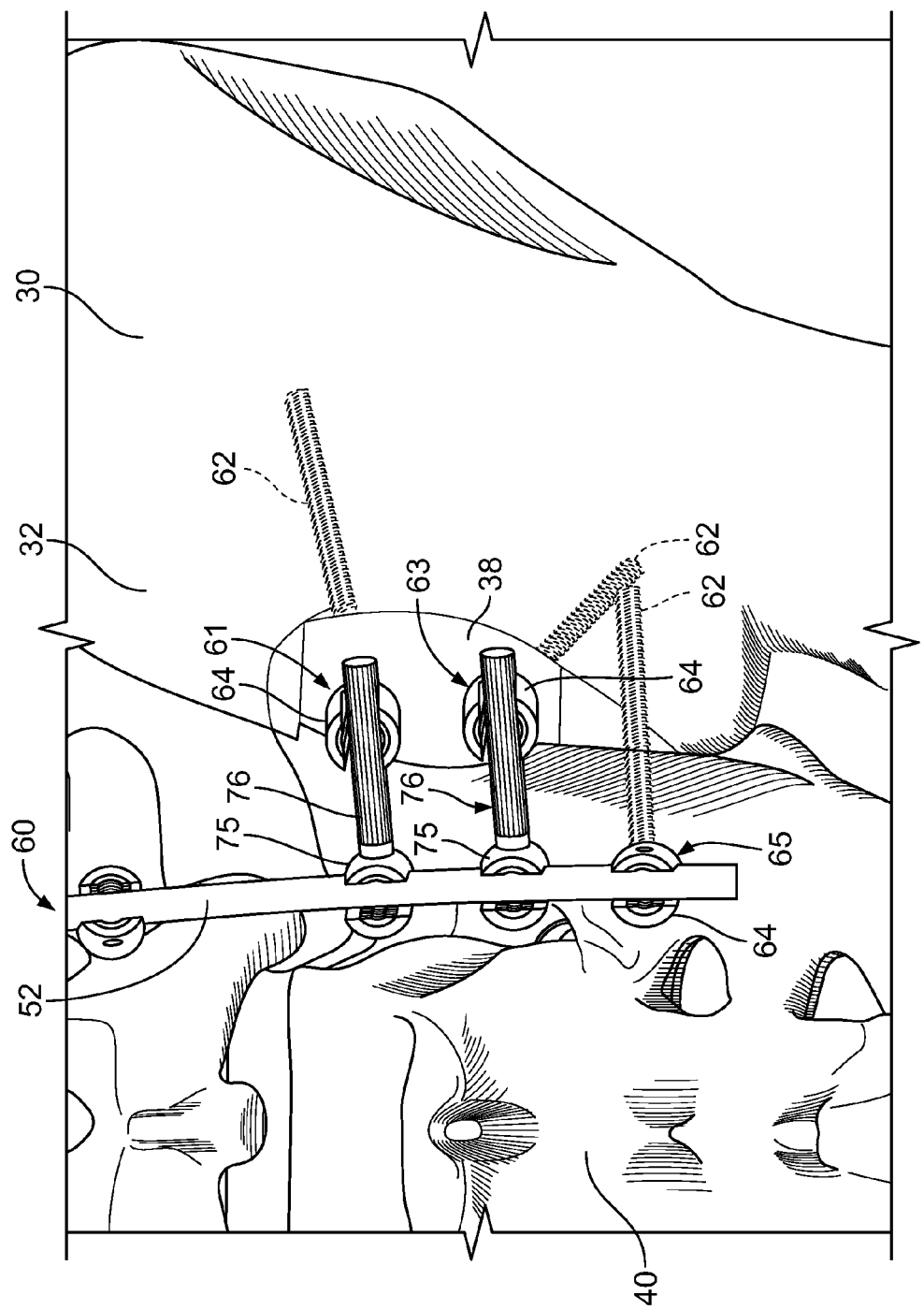
Figure 13:
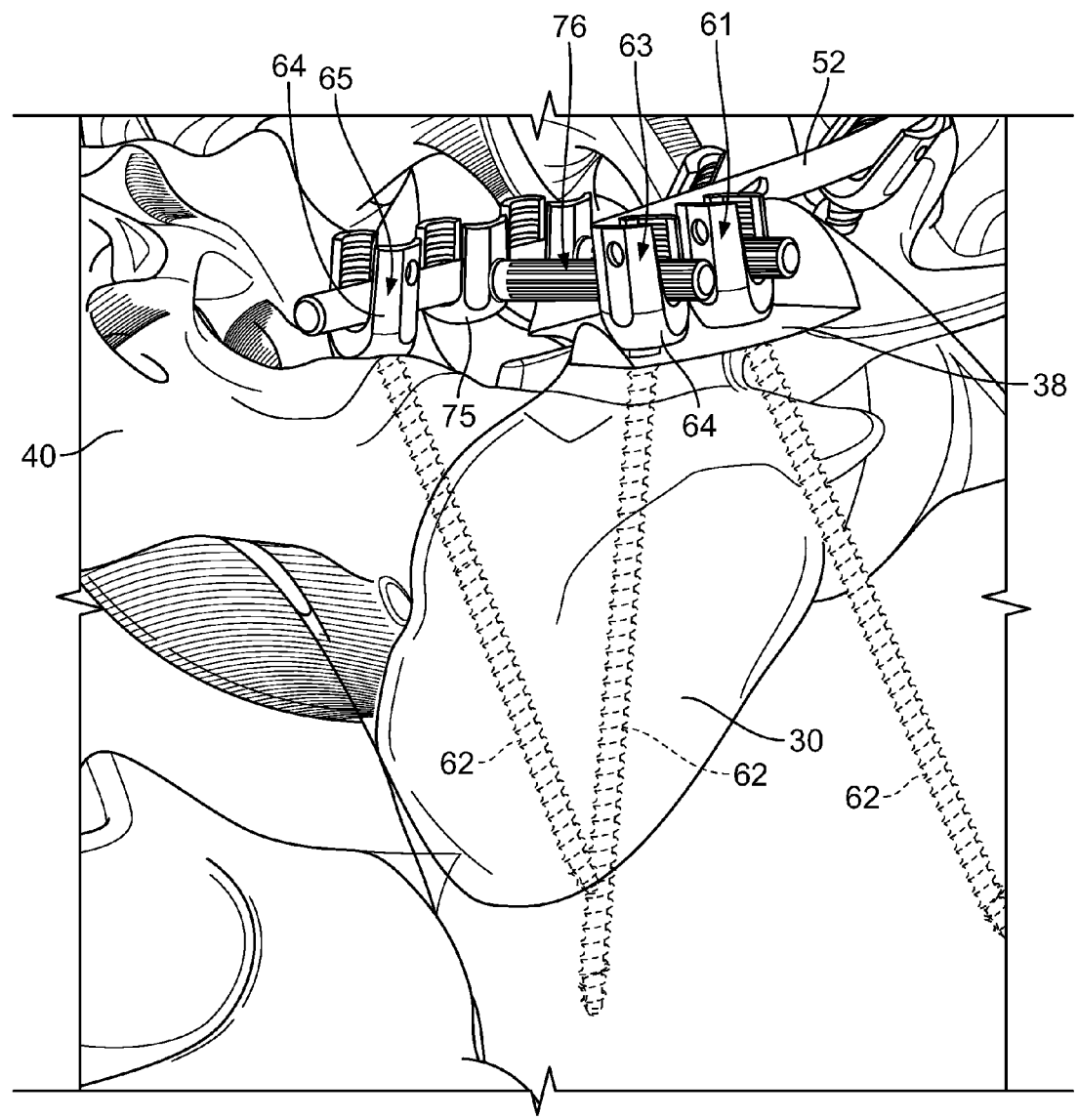

Referring to FIGS. 9-13, after the iliac and sacral bores 150, 152, 154 have been formed using the universal guide 100, 100', the universal guide 100, 100' is removed from the pelvis and preoperatively selected and determined portions 37 of the iliac crests 32 can be resected to create a planar recess or seat 38 to accommodate the receivers 64 of the first and second iliac screw assemblies 61, 63 shown in FIGS. 11-13.

Referring to FIGS. 6-8, the iliac guide 100A, sacral guide 100B and unilateral guide 100C are more specialized versions of the universal guide 100, 100'. The iliac guide 100A, as shown in FIG. 6, is similar to the universal guide 100 shown in FIG. 5, but with the sacral guiding elements 130 omitted. It will be appreciated, however, that in other embodiments, the iliac guide 100A can be arranged as the universal guide 100' shown in FIG. 5A, but with the sacral guiding elements 130 omitted.

The sacral guide 100B, as shown in FIG. 7, is similar to the universal guide 100 shown in FIG. 5, but with the iliac guiding elements 122, 124 omitted. It will be appreciated, however, that in other embodiments, the sacral guide 100B can be arranged as the universal guide 100' shown in FIG. 5A, but with the iliac guiding elements 122, 124 omitted.

The unilateral guide 100C, as shown in FIG. 8, is similar to the one side (left side is shown) of the universal guide 100' shown in FIG. 5A, without the bridge 104 and without the sacral guiding element 130. It will be appreciated, however, that in other embodiments, the unilateral guide 100C can be arranged as the universal guide 100 shown in FIG. 5, without the bridge 104 and without the sacral element 130. The unilateral guide 100C, as shown in FIG. 8, is a left side iliac unilateral guide. A right side iliac unilateral guide can be similarly constructed. Additionally, unilateral (left or right side) sacral guides can be constructed by using the arrangement of the sacral guide 100B shown in FIG. 7 without the bridge 104 and without the opposite side patient-specific portion 102.

Although various separate patient-specific unilateral, iliac and sacral can be constructed for a specific patient and surgeon, the patient-specific universal guide 100, 100' forms a bilateral sacroiliac guide that can be utilized intraoperatively to cover any intraoperative change in plan or intraoperative event for the specific patient. For example, if the surgeon decides to only do a unilateral fixation using sacral and/or iliac bone screws on the left (right) side only, then the corresponding iliac and/or sacral guiding elements of the opposite right (left) side can simply not be used (no drilling on that side). In this respect, removable plugs or covers can be provided in all or some of the guiding elements, such that attention is directed to which guiding elements should be used by positively removing the plugs and exposing the corresponding guiding openings.

Another option is to decouple the bridge 104 and the right (left) side of the universal guide 100, 100' from the left (right) side and completely remove it. Similarly, the universal guide 100, 100' can be used for iliac fixation only or for sacral fixation only by not using or by removing those iliac or sacral guiding elements that are not needed. Additionally, the universal guide 100, 100' can be fully modular, as described above, and constructed as a bilateral sacroiliac guide with a removable bridge 104 and removable iliac and sacral guiding elements 122, 124, 130 and/or arms 132. The modular universal guide 100, 100' is intraoperatively convertible and reconfigurable at the discretion of the operating surgeon. Accordingly, the same universal patient-specific guide 100, 100' can be used in several different fixation options of the same patient. As these fixation options are changed or selected intraoperatively, the modular universal guide 100, 100' provides the surgeon with intraoperative flexibility, reconfigurability and adaptability to an intraoperative change of plan and surgical procedure informed by intraoperative and possibly unanticipated circumstances. Color-coding and raised or embossed markings indicating size, orientation or other relevant information, such as, for example, patient identification, guide or element type and position, can help streamline intraoperative assembling, positioning and use and help avoid errors. At the same time, and regardless of the fixation option selected, the features and advantages of using a patient-specific guide are retained.

The universal guide 100, 100' (or the iliac guide 100A, or the sacral guide 100B, or the unilateral guide 100C) is removed from the pelvis after the bone bores (150, 152, 154) for the selected fixation procedure have been drilled into the bone. The bone bores (150, 152, 154) are used to guide corresponding bone screw assemblies of a selected fixation system 50 according to the surgical technique associated with the fixation system.

Example embodiments are provided so that this disclosure is thorough, and fully conveys the scope to those who are skilled in the art. Numerous specific details are set forth, such as examples of specific components, devices, and methods, to provide a thorough understanding of embodiments of the present disclosure.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An orthopedic device comprising:
    a patient-specific alignment guide including:
        first and second patient-specific portions, each portion having a patient-specific surface preoperatively configured to mate as a negative of a respective portion of an iliac crest of a pelvis of a specific patient and mate to the respective portion of the iliac crest only in one position;
        first and second iliac guiding elements connected to the first and second patient-specific portions, respectively, at first releasable connections such that the entire first and second iliac guiding elements can be detached from the first and second patient-specific portions, each iliac guiding element having a through opening and a preoperatively configured orientation and location relative to the respective first or second patient-specific portion for drilling a bone bore in the bone of the patient from the iliac crest of the patient into an iliac wing of the patient to direct a bone screw at the preoperatively configured orientation and location for sacroiliac fixation; and
        a bridge connected to both of the first and second patient-specific portions at second releasable connections.

2. The orthopedic device of claim 1, further comprising first and second sacral guiding elements coupled to the first and second patient-specific portions via third releasable connections at the bridge, the first and second sacral guiding elements configured for drilling a bone bore from a sacrum into an iliac wing of the patient.

3. The orthopedic device of claim 2, wherein the first and second sacral guiding elements are connected to first and second arms, respectively, that are connected to the third releasable connections at the bridge.

4. The orthopedic device of claim 1, wherein the bridge includes an opening configured to receive a pin referencing a sacral process.

5. The orthopedic device of claim 1, further comprising a fixation guiding element configured for securing the alignment guide on the pelvis.

6. The orthopedic device of claim 1, wherein the bridge is arch-shaped and connects to the first and second patient-specific portions to span a posterior contour of the sacrum of the pelvis of the patient between iliac crests without engaging a boney structure of the pelvis of the patient.

7. The orthopedic device of claim 1, wherein the second releasable connections between the bridge and the first and second patient-specific portions comprise taper-to-taper connections.

8. The orthopedic device of claim 1, wherein the first releasable connections between the first and second iliac guiding elements and the first and second patient-specific portions, respectively, comprise bayonet connections.

9. An orthopedic device for guiding sacroiliac fixation comprising:
    a first patient-specific portion having a first patient-specific surface preoperatively configured to nestingly mate to a portion of a first iliac crest of a pelvis of a specific patient and mate to the first iliac crest only in one position,
    a second patient-specific portion having a second patient-specific surface preoperatively configured to mate to a portion of a second iliac crest of a specific patient and mate to the second iliac crest only in one position,
    an arcuate elongated bridge coupling the first and second patient-specific portions via first releasable couplings, the bridge configured to span a posterior contour of the sacrum of the pelvis of the patient between the first and second iliac crests;
    first and second iliac guiding elements coupled to the corresponding first and second patient-specific portions via second releasable couplings;

first and second sacral guiding elements coupled to the bridge via third releasable couplings; and wherein each of the first and second iliac and sacral guiding elements has a through opening and a preoperatively configured orientation and location relative to one of the first and second patient-specific portions for preparing a corresponding bore in the bone of the patient to direct a corresponding bone screw for lumbopelvic fixation.

10. The orthopedic device of claim 9, further comprising a fixation guiding element for securing the orthopedic device to the pelvis of the patient.

11. The orthopedic device of claim 9, wherein the bridge includes an opening preoperatively configured for receiving a locating pin referencing a sacral process of the patient.

12. The orthopedic device of claim 9, wherein the first and second sacral guiding elements are coupled to corresponding first and second arms extending from the bridge at the third releasable couplings.

13. The orthopedic device of claim 12, wherein the third releasable couplings comprise taper-to-taper connections.

14. The orthopedic device of claim 9, wherein the first releasable couplings comprise taper-to-taper connections.

15. The orthopedic device of claim 9, wherein the second releasable couplings comprise bayonet connections.

16. The orthopedic device of claim 9 in combination with a spinal fixation system including a plurality of multiaxial bone screw assemblies and elongated fixation members.

17. The orthopedic device of claim 9 wherein the bridge is shaped to provide a gap between the bridge and the sacrum to provide a handle to facilitate placement of the orthopedic device.

* * * * *